United States Patent
Tungare et al.

(10) Patent No.: US 10,747,315 B2
(45) Date of Patent: *Aug. 18, 2020

(54) COMMUNICATION AND CONTROL SYSTEM AND METHOD

(71) Applicant: TECHNOLOGY AGAINST ALS, Parsippany, NJ (US)

(72) Inventors: Sandeep Tungare, Morristown, NJ (US); Milind Gupte, Boonton, NJ (US); Amitabh Patil, Princeton, NJ (US); Naveen Reddy, South Orange, NJ (US); Bert Haberland, Succasunna, NJ (US)

(73) Assignee: Technology Against ALS, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/502,112

(22) Filed: Jul. 3, 2019

(65) Prior Publication Data
US 2019/0324535 A1 Oct. 24, 2019

Related U.S. Application Data

(63) Continuation of application No. 15/027,731, filed as application No. PCT/US2014/063162 on Oct. 30, 2014, now Pat. No. 10,372,204.
(Continued)

(51) Int. Cl.
*G06F 3/01* (2006.01)
*A61F 4/00* (2006.01)
(Continued)

(52) U.S. Cl.
CPC ............. *G06F 3/013* (2013.01); *A61F 4/00* (2013.01); *G02B 27/0093* (2013.01); *G02B 27/01* (2013.01); *G02B 27/017* (2013.01); *G06F 3/015* (2013.01); *G06F 3/017* (2013.01); *G06F 3/0236* (2013.01); *G06F 3/0237* (2013.01); *G06F 3/0487* (2013.01); *G06F 3/04842* (2013.01); *G06F 3/167* (2013.01); *G09B 21/00* (2013.01);
(Continued)

(58) Field of Classification Search
CPC ........ G06F 3/013; G06F 3/0236; G06F 3/015; G06F 3/0237; G06F 3/167; G06F 3/0487; G06F 3/017; G06F 3/04842; G02B 27/0093; G02B 27/017; G02B 27/01; G02B 2027/0187; G02B 2027/0141; G02B 2027/0178; A61F 4/00; G09B 21/00
See application file for complete search history.

(56) References Cited

U.S. PATENT DOCUMENTS 6,005,549 A     12/1999  Forest
9,129,430 B2 *   9/2015  Salter .................. G06F 3/013
(Continued)

FOREIGN PATENT DOCUMENTS

WO       2013133618 A1      9/2013

*Primary Examiner* — Jose R Soto Lopez
(74) *Attorney, Agent, or Firm* — Duane Morris LLP

(57) ABSTRACT

An input system includes at least one sensor and a controller communicatively coupled to the at least one sensor. The at least one sensor is configured to identify a position of an eye. The controller is configured to receive a first signal indicative of a first position of an eye from the at least one sensor and map the eye position to a user's selection.

20 Claims, 29 Drawing Sheets

Related U.S. Application Data

(60) Provisional application No. 61/897,529, filed on Oct. 30, 2013.

(51) Int. Cl.
| | |
|---|---|
| *G06F 3/0487* | (2013.01) |
| *G02B 27/01* | (2006.01) |
| *G09B 21/00* | (2006.01) |
| *G06F 3/0484* | (2013.01) |
| *G02B 27/00* | (2006.01) |
| *G06F 3/023* | (2006.01) |
| *G06F 3/16* | (2006.01) |

(52) U.S. Cl.
CPC ............ *G02B 2027/0141* (2013.01); *G02B 2027/0178* (2013.01); *G02B 2027/0187* (2013.01)

(56) References Cited

U.S. PATENT DOCUMENTS

| | | | | |
|---|---|---|---|---|
| 2004/0174496 A1* | 9/2004 | Ji | ............................ | G06F 3/013 351/209 |
| 2008/0266596 A1* | 10/2008 | Sato | ...................... | G06F 3/1204 358/1.15 |
| 2010/0057645 A1* | 3/2010 | Lauritsen | ............... | G06N 5/042 706/11 |
| 2010/0100849 A1 | 4/2010 | Fram | | |
| 2010/0110368 A1* | 5/2010 | Chaum | ................ | G02B 27/017 351/158 |
| 2011/0205242 A1* | 8/2011 | Friesen | ................ | A43B 3/0078 345/633 |
| 2012/0019662 A1* | 1/2012 | Maltz | ...................... | G06F 3/013 348/158 |
| 2012/0105486 A1* | 5/2012 | Lankford | ................ | G06F 3/013 345/661 |
| 2012/0263449 A1* | 10/2012 | Bond | ..................... | G03B 17/48 396/420 |
| 2012/0278747 A1* | 11/2012 | Abraham | ................ | G06F 9/452 715/771 |
| 2013/0007668 A1* | 1/2013 | Liu | .......................... | G06F 3/012 715/841 |
| 2013/0024047 A1* | 1/2013 | Kalhous | .................. | G06F 3/013 701/1 |
| 2013/0132885 A1* | 5/2013 | Maynard | ............. | G06F 3/04883 715/777 |
| 2013/0135196 A1* | 5/2013 | Park | .......................... | G06F 3/01 345/156 |
| 2013/0176626 A1* | 7/2013 | Heinrich | ............... | G02B 27/017 359/630 |
| 2013/0207964 A1* | 8/2013 | Fleck | ...................... | F21V 5/004 345/419 |
| 2013/0295994 A1* | 11/2013 | Guitteaud | .............. | F16M 13/00 455/556.1 |
| 2014/0049558 A1* | 2/2014 | Krauss | .................... | G06F 3/011 345/633 |
| 2014/0125789 A1* | 5/2014 | Bond | .................... | G02B 27/017 348/77 |
| 2014/0304642 A1* | 10/2014 | Santos | .................... | G06F 16/48 715/780 |
| 2014/0325425 A1* | 10/2014 | Milam | .................. | G06F 3/0482 715/777 |
| 2014/0333665 A1 | 11/2014 | Sylvan | | |
| 2015/0009313 A1* | 1/2015 | Noda | .................... | A61B 5/1171 348/78 |
| 2015/0049112 A1* | 2/2015 | Liu | ........................ | G06T 19/006 345/633 |
| 2015/0070470 A1* | 3/2015 | McMurrough | ......... | G06F 3/013 348/46 |
| 2015/0103003 A1* | 4/2015 | Kerr | ....................... | G06F 3/013 345/158 |
| 2015/0317069 A1 | 11/2015 | Clements | | |
| 2016/0092062 A1* | 3/2016 | Miyagi | ................. | G06F 3/0488 345/173 |
| 2016/0188181 A1* | 6/2016 | Smith | ..................... | G06F 3/045 715/765 |
| 2016/0195924 A1* | 7/2016 | Weber | .................. | G06F 3/0304 345/156 |
| 2017/0139567 A1* | 5/2017 | Li | ......................... | G06F 3/0487 |

* cited by examiner

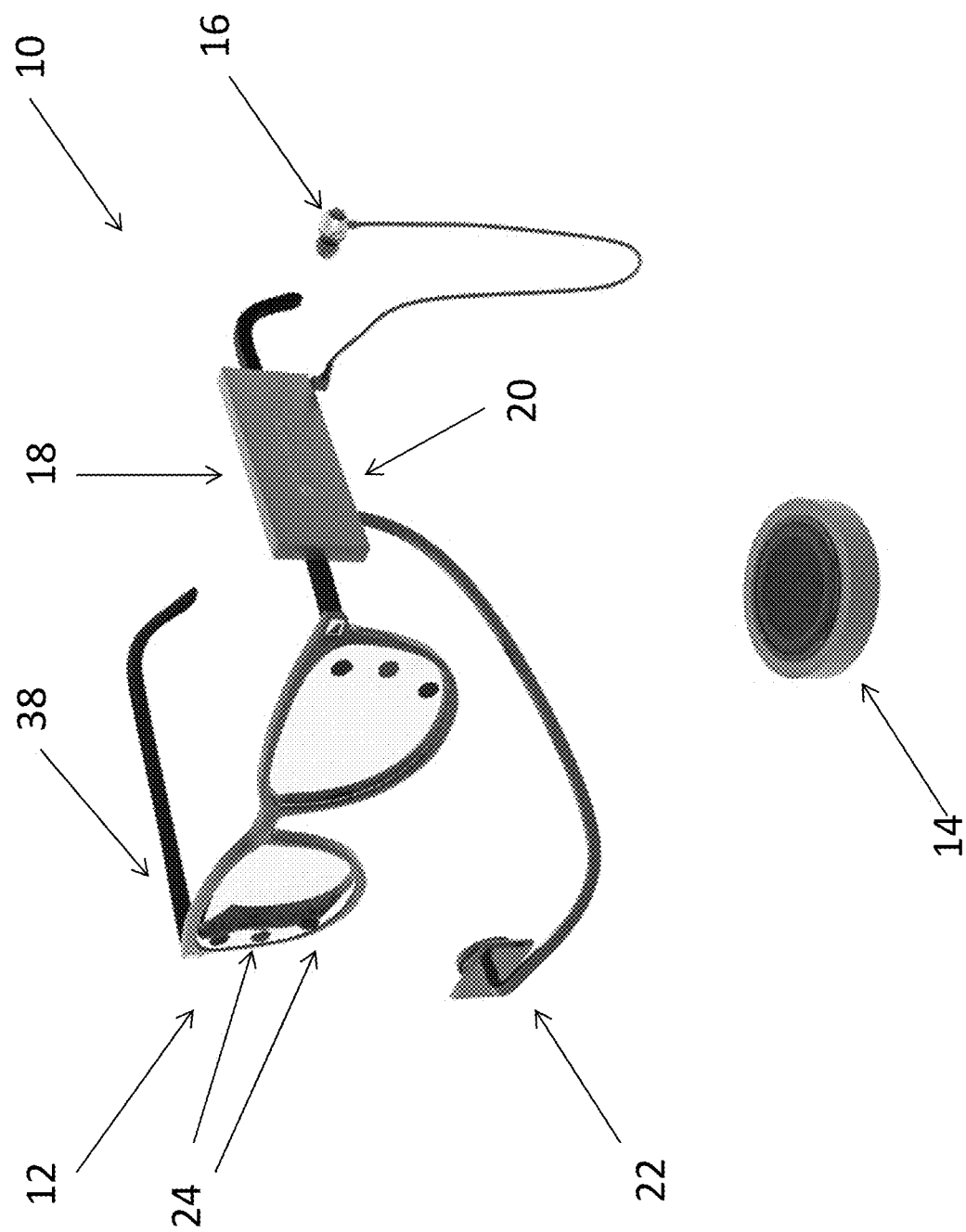

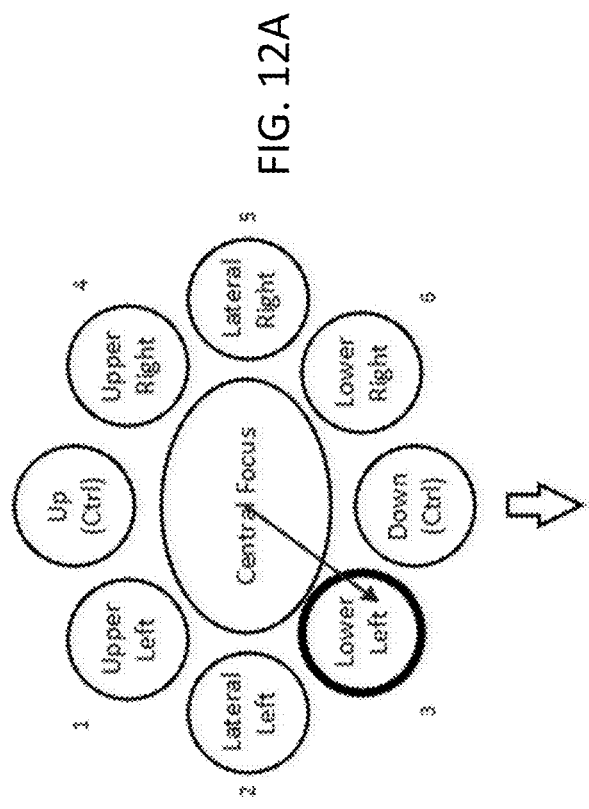
FIG. 12A
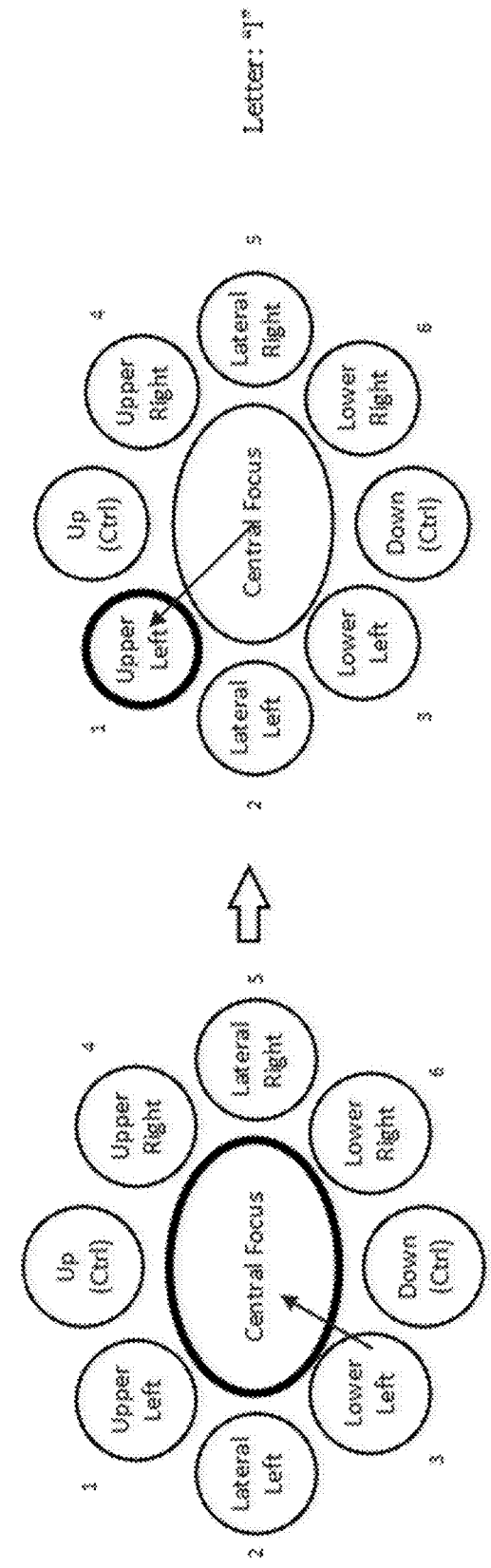
FIG. 12B
FIG. 12C

COMMUNICATION AND CONTROL SYSTEM AND METHOD

CROSS-REFERENCE TO RELATED APPLICATIONS

This application is a continuation application of U.S. patent application Ser. No. 15/027,731, filed Apr. 7, 2016, which claims priority to U.S. Provisional Patent Application Ser. No. 61/897,529, filed Oct. 30, 2013, the entireties of which are incorporated herein by reference.

FIELD OF DISCLOSURE

The disclosed systems and methods relate to wearable electronics. More particularly, the disclosed systems and methods relate to wearable, hands-free communication systems and methods.

BACKGROUND

Augmentative and Alternative Communication (AAC) devices enable individuals with difficulty communicating, such as patients with Amyotrophic Lateral Sclerosis (ALS) and Locked-in Syndrome (LIS), to communicate and control their environment.

Conventional AAC devices are large and obtrusive. Further, they require complex devices or software that need frequent calibrations and adjustments to account for any head or body movements. Since the Communicator is head-mounted, once the device is calibrated for the user no further calibrations should be necessary.

BRIEF DESCRIPTION OF THE DRAWINGS

FIGS. 1A-F illustrate various examples of a communication system in accordance with some embodiments.

FIGS. 12A-12C illustrate one example of a method of using eye movements in a sequence to make a selection on a communication board in accordance with some embodiments.

DETAILED DESCRIPTION

Figure 1A:
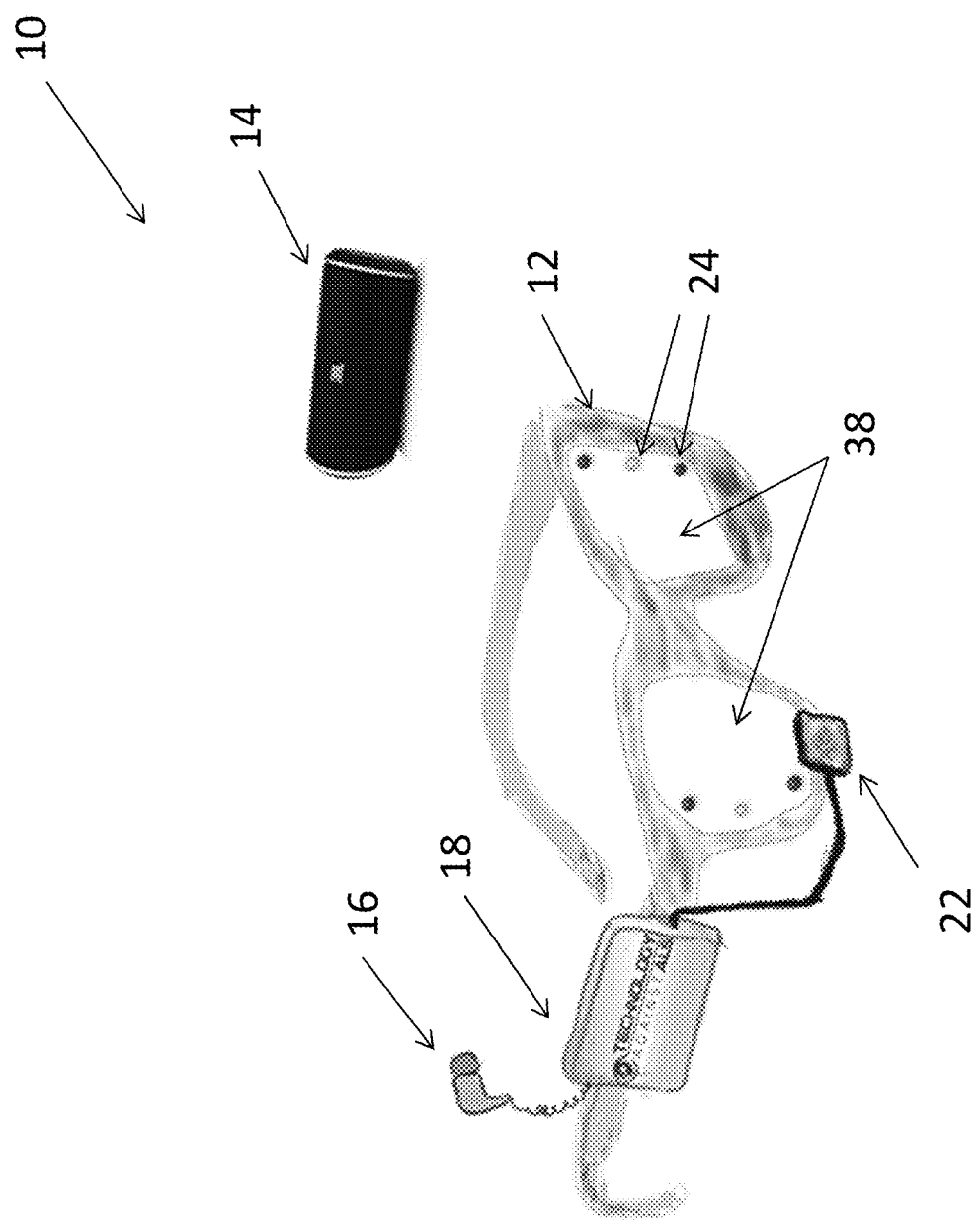

This description of the exemplary embodiments is intended to be read in connection with the accompanying drawings, which are to be considered part of the entire written description.

In some embodiments, the communication system includes a low-cost, portable, standalone Augmentative and Alternative Communication ("AAC") device that enables patients with ALS or other disabilities or impairments to communicate, i.e., by generating speech or text, with the external environment using eye movement as input to the device. However, the disclosed systems and methods disclosed herein can be extended to provide an input system for controlling one or more other systems through the movement of an eye, a user's breath, or other movement of a human body excluding an appendage such as a hand, foot, or limb.

The systems described herein comprise easy to use wearable devices that can be used with, but do not require, any display components. Instead, in some embodiments, selection feedback is provided by audio via an earpiece worn by the user or another feedback mechanism. In some embodiments, visual feedback is provided by multi-colored light-emitting diodes ("LEDs") mounted around the user's field of vision or through other optical means. Advantageously, the disclosed devices are small, lightweight, and enable users to see the audience with whom the user is communicating without the user's vision being obscured by large, bulky components like conventional AAC systems. Further, the disclosed devices are able to work unobtrusively without requiring a bedroom or hospital setting. For example, in some embodiments, the devices work in "non-controlled settings," such as while travelling in a wheelchair and/or a handicapped accessible vehicle.

In some embodiments, the device is able to achieve speech rates, in one or more languages, between 15-20 words per minute ("WPM") using suggestions, completions, and templates based on computer algorithms and preloaded dictionaries. One of ordinary skill in the art will understand that lower or higher rates of speech also are possible and contemplated herein.

Advantageously, the disclosed systems and methods are easy to use such that a user can use the device with minimal training for communicating basic needs and short sentences. In some embodiments, a self-directed learning tutorial is installed on the device to facilitate the user's training. Further, because the devices are head-mountable and able to located at a substantially constant position relative to a user's eye, the devices do not require extensive calibration.

Beyond providing communication, the disclosed systems and methods can be used for controlling and interacting with the external environment. For example, a user can signal intent in the same way it can communicate using the disclosed systems: the user selects an event using based on the movement or position of an eye, which is sensed by one or more sensors that communicate the eye position to a controller. The one or more signals transmitted to the controller from the one or more sensors is mapped to a predetermined intent by controller, which then facilitates or completes an action. Regarding controlling and interacting with the external environment, these actions could include, but are not limited to: controlling a television, controlling medical support devices such as a motorized bed or wheelchair, and controlling lights in a room, to list only a few possibilities.

FIGS. 1A-F illustrate various, non-limiting examples of a communication system 10. In some embodiments, the system 10 comprises a wearable support structure 12 that can take a variety of forms. In the embodiment illustrated in FIG. 1A, for example, support structure 12 is provided as a pair of eyeglass frames. However, support structure can take a variety of other forms including, but not limited to, a headband, a monocle, a hat, a structure that clips on to eyeglass frames, a headset or other wearable frame that can support one or more of the additional components of system 10.

Figure 1B:
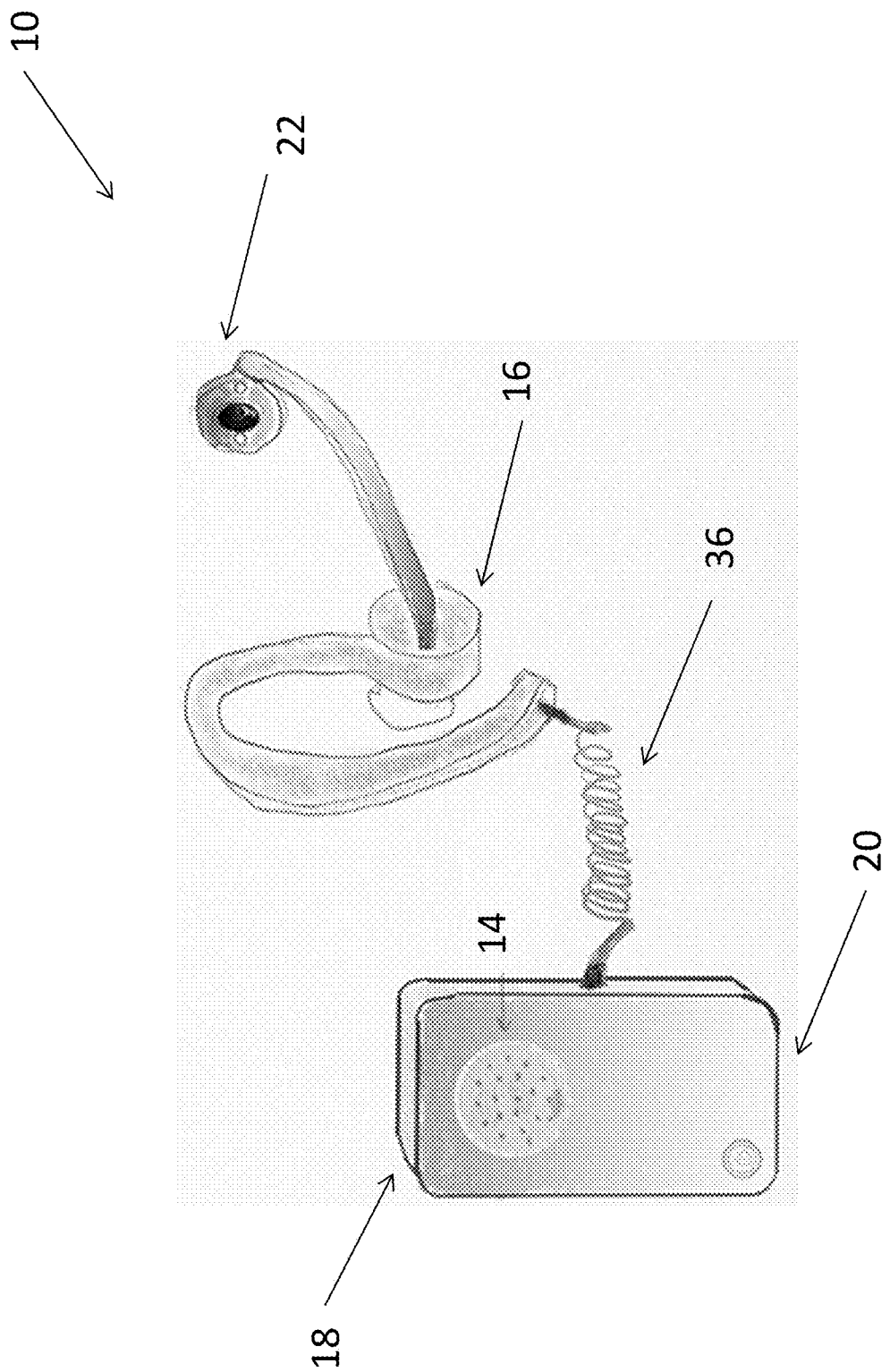
Figure 1D:
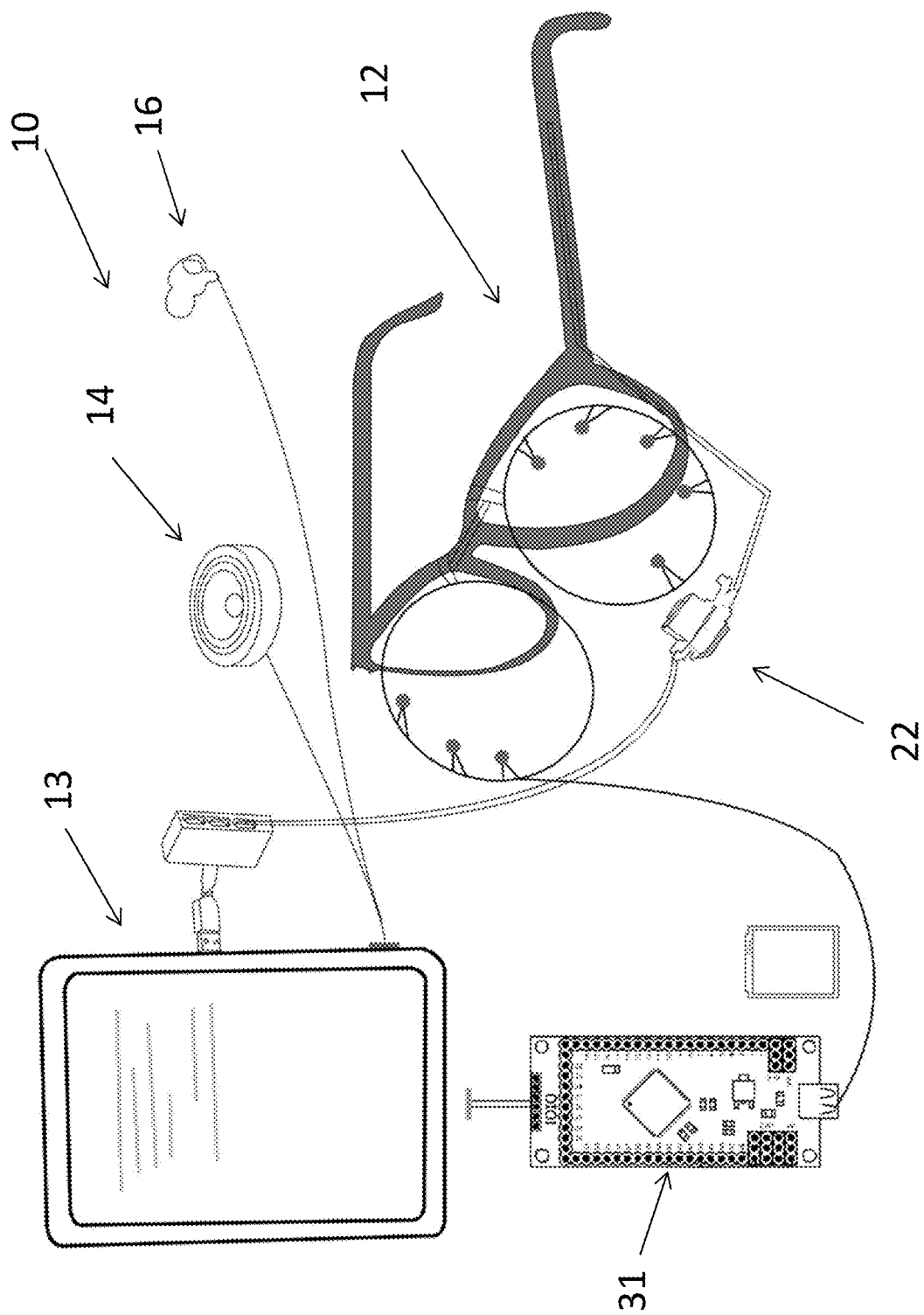

In some embodiments, system 10 is further configured with a first feedback mechanism 14, e.g., a speaker, and a second feedback mechanism 16, e.g., an earpiece, a controller 18, which includes a processor 21 and battery 20, and an eye tracker 22. In some embodiments, a tablet 13 can serve as a display monitor 17 and processor 21, as illustrated in FIG. 1D. The tablet 13 can also serve as a battery 20, and speaker 14.

Figure 1E:
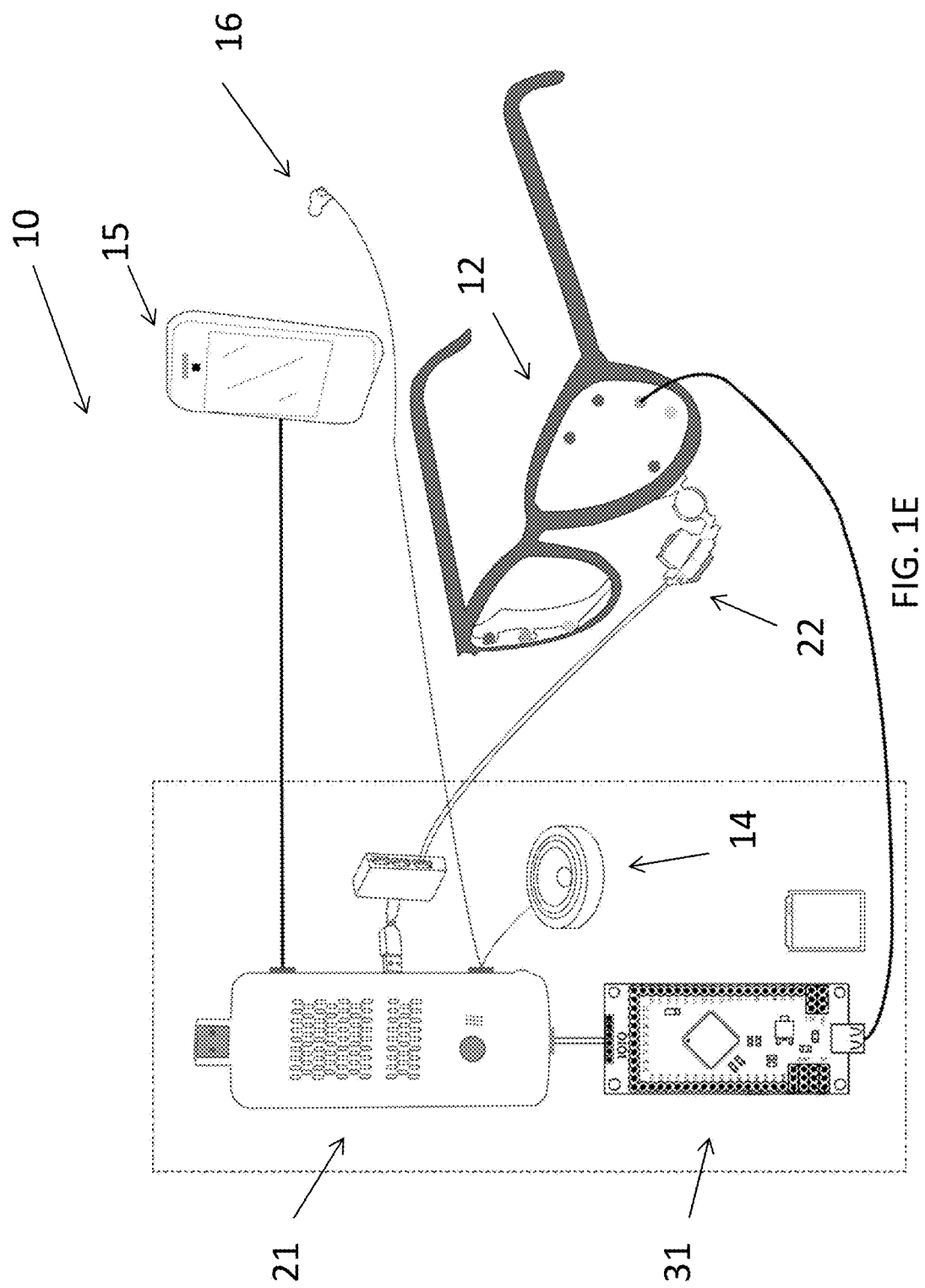

In some embodiments, the processor 21 can be configured with a port to connect either wirelessly or through a wired connection to a phone 15, as illustrated in FIG. 1E. The phone 15 can then serve as a display monitor 17.

Figure 1F:
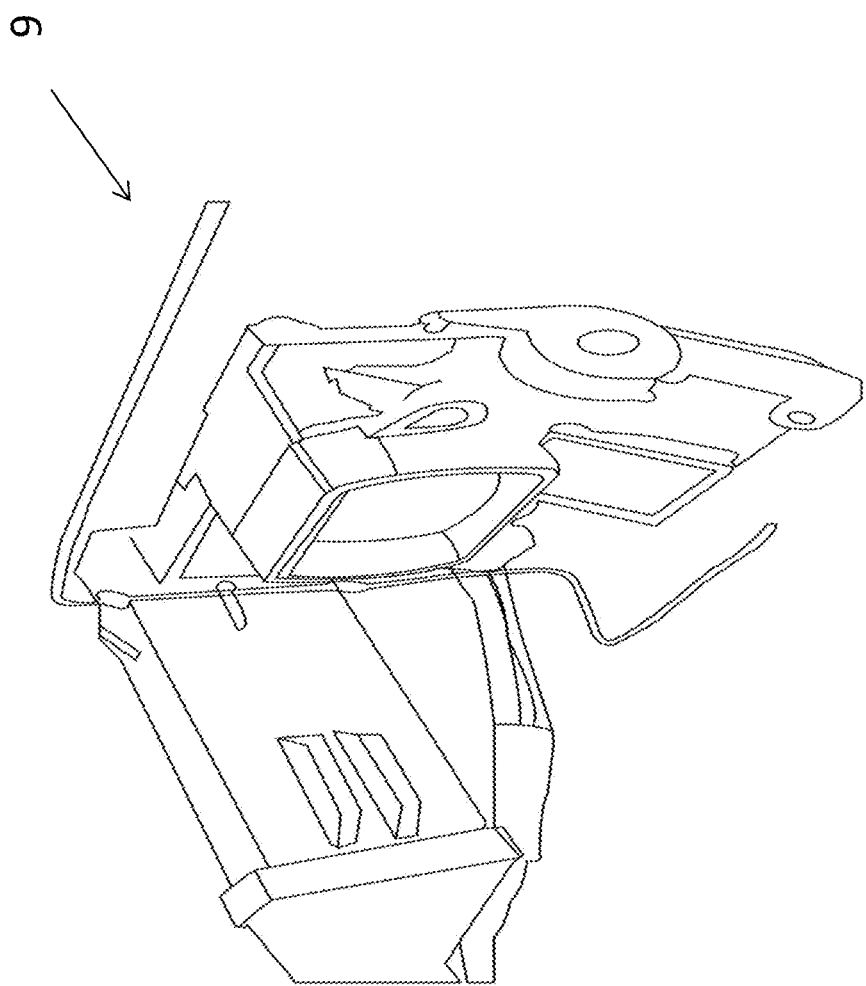

The second feedback mechanism 16 may also be visual feedback mechanisms, such as mounted colored LED lights in varying directions, which can change in brightness, intensity, duration of LED blinks, and number of blinks; optical fiber connected to LEDs; a mounted Heads Up Display (HUD) 9 which can display information right in front of the eye as illustrated in FIG. 1F, thereby enabling the user to view information without breaking their line of sight; a television screen or monitor, such as an LCD monitor, which can be connected via a wired or wireless connection to the controller 18; or a non-mounted display. Additionally, an LCD monitor with a touch screen can also be used as an input/output option.

In some embodiments, the battery 20, can be separate from the controller 18. One example of the hardware components of the communication system 10 are illustrated in FIG. 2. Additionally, although an eye tracker 22 is disclosed, motion sensing circuitry that is head mounted can also be used to track head movements. Breath sensors, accelerometers, moisture sensors and infrared muscle movement detectors can be used as well.

Figure 2A:
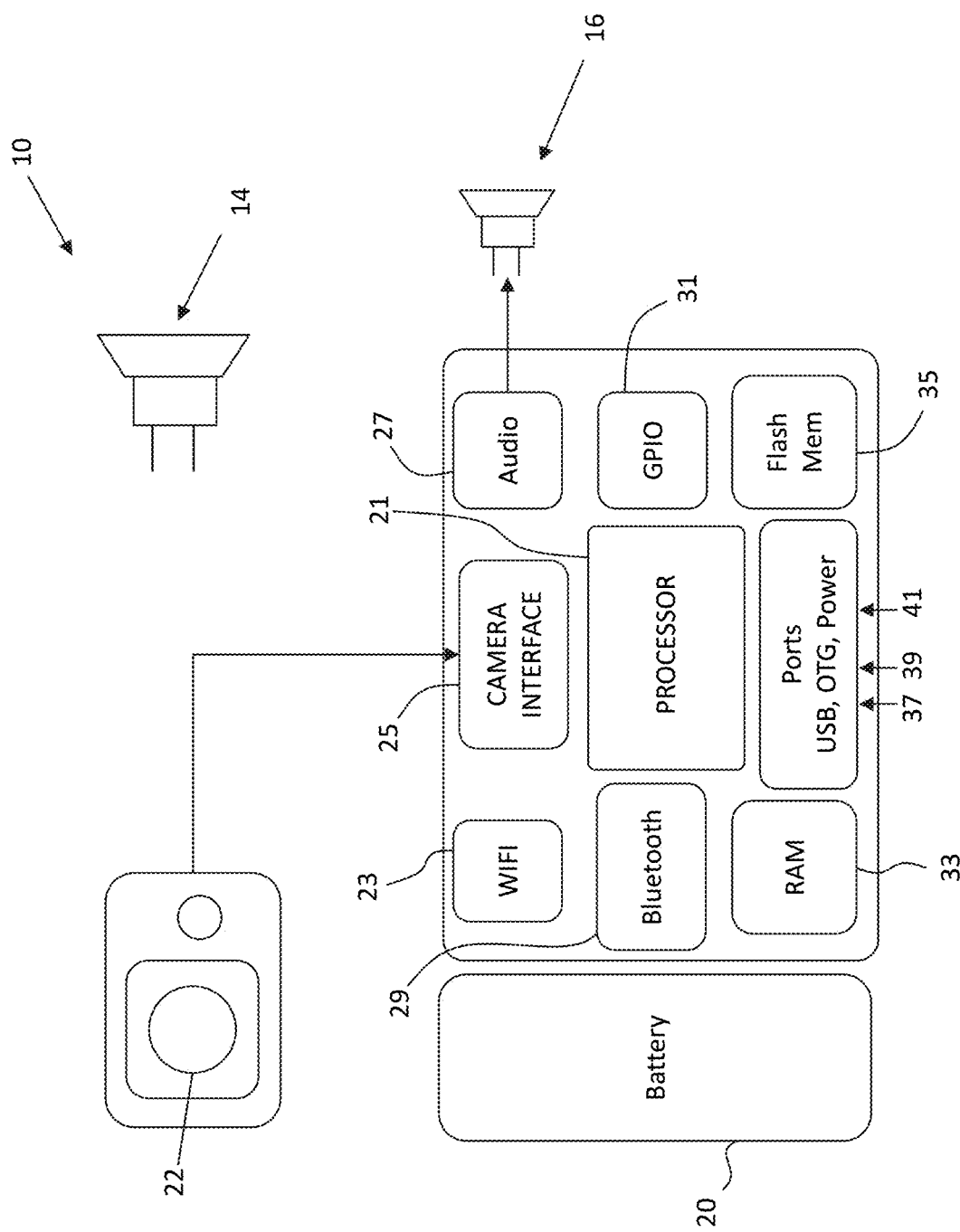
FIGS. 2A-B illustrate hardware components of the communication system in accordance with some embodiments.
Figure 2B:
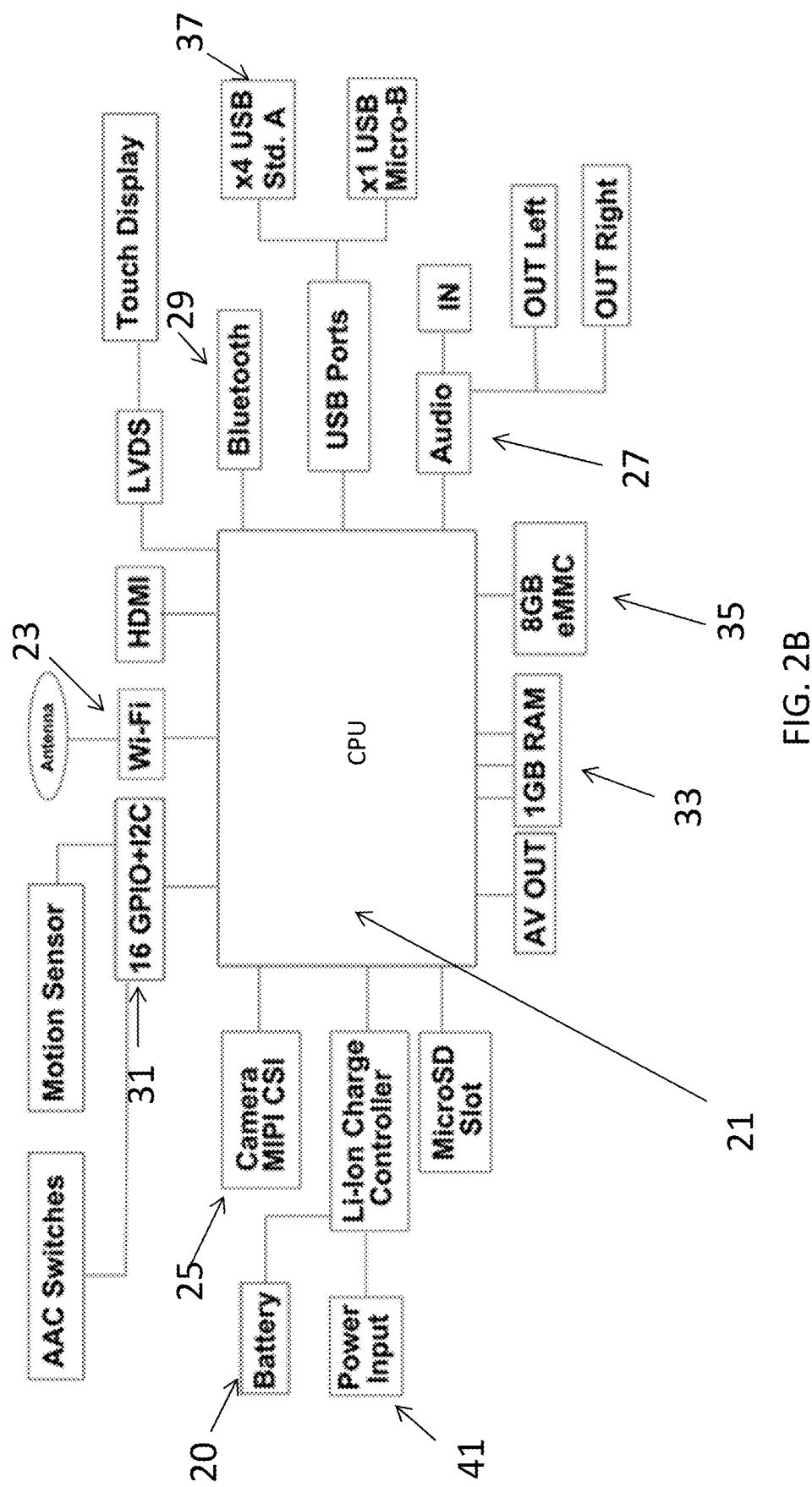

As shown in FIGS. 2A-B, in some embodiments, the controller 18 comprises one or more processors 21 (such as a single core or multi-core processor), a first wireless communication (e.g., WiFi) chip 23, a camera interface 25, an audio interface 27, a Bluetooth chip 29, a general purpose input/output pin 31, a first memory 33, a second memory 35, a Universal Serial Bus (USB) port 37, a USB On the Go port 39, and a power port 41. In some embodiments, the processor 21 is connected to each of the different chips, including the Bluetooth chip 29, first wireless communication chip 23, audio interface 27 and camera interface 25. The camera interface 25 enables communication between the processor 21 and the eye tracker 22. The audio interface 27 enables communication between the processor 21 and the second feedback mechanism 16. The Bluetooth chip 29 enables communication between the processor 21 and the first feedback mechanism 14. The general purpose input/output pin (GPIO) 31 is a generic pin whose performance, including whether it is an input or output pin, can be determined by the user. GPIO pin 21 also can be used to connect the controller 18 to the LED lights. The USB port 37 allows a USB cable to connect to the controller 18. The USB On the Go port 39 enables the controller 18 to act as a host, where other USB devices are connected to it and enables host and device role swapping within the connection. The power port 41 allows the controller 18 to connect to a power source. The first memory 33 may be a random access ("RAM") memory. The second memory 35 may be non-volatile storage that does not require power to retain data, such as Negated AND or NOT AND (NAND) flash memory. In some embodiments, the controller 18 is arranged as a module comprising a plurality of chips, such as in the arrangement shown in FIGS. 5A-B.

In some embodiments, the first feedback mechanism 14 is a rechargeable Bluetooth (or other wireless) enabled speaker supporting A2DP protocol. The first feedback mechanism 14 is used for final speech output and communicating with other people. In some embodiments, the first feedback mechanism 14 is implemented with a wired connection 36, as illustrated in FIG. 1B. Feedback mechanism 14, as described in greater detail below, is configured to output speech signals generated by controller 18. In some embodiments, the first feedback mechanism's 14 primary function is to communicate the generated speech signals to a person communicating with the user. However, one of ordinary skill in the art will understand that feedback mechanism 14 can provide any number of functions beyond communicating the generated speech to a person communicating with the user.

Figure 3:
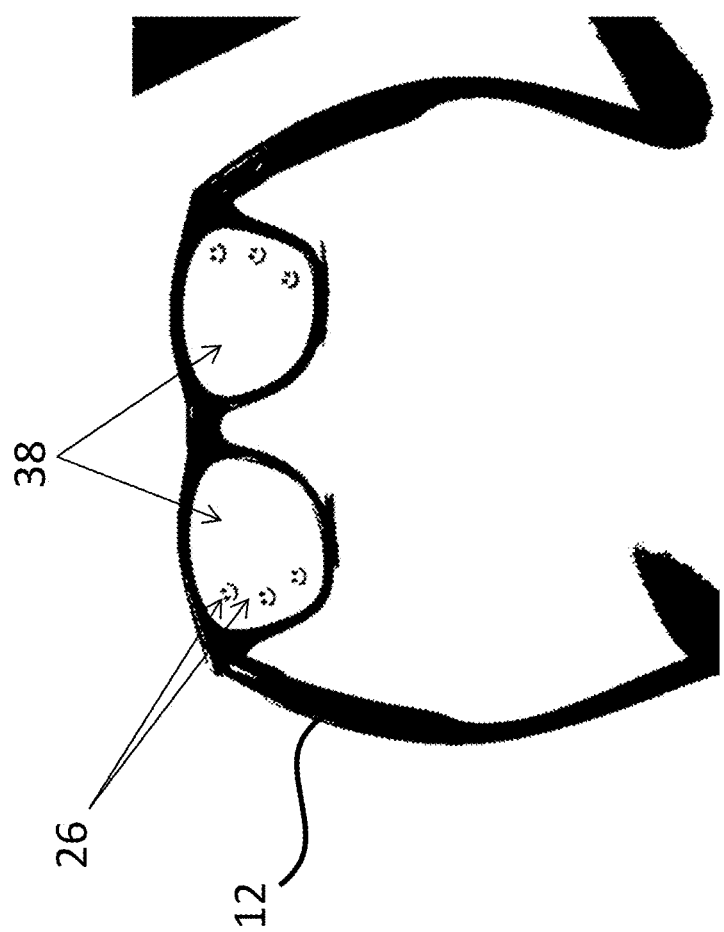
FIG. 3 is a posterior view of glasses with gaze spots in a communication system in accordance with some embodiments.

Referring again to FIG. 1A, the support structure 12 includes a pair of glass frames 38 configured to position a plurality of visual indicia such as points or gaze spots 24 for a user to gaze towards to make selections and interface with the communication system. As illustrated in FIG. 3, the points 24 may be marked using small stickers 26; however, these points can be implemented in other ways including, but not limited to, being painted, etched, projected, or adhered to the glass supported by frame 38. For example, in some embodiments, light, such as from LEDs or other light generating means, is projected in a user's field of vision. The markings may be in the form of dots or other graphical indicia. For a more trained user, the markings may be removed.

Referring again to FIG. 1A, second feedback mechanism 16 is coupled to controller 18 (either via wires or wirelessly) and is configured to output audible signals. For example, second feedback mechanism 16 is configured to output an audio feedback, such as a beep or musical note, when the eye tracker 22 detects user gaze or fixation to one of the gaze spots 24. The second feedback mechanism 16 may be a standard mono earpiece with 3.5 mm audio jack. The second audio device 16 can be used as a listening device through which the user hears audio feedback. In some embodiments, second feedback mechanism 16 is configured to be received at least partially in, and be supported by, a user's ear. However, in some embodiments, earpiece 16 can take other forms, such as a pair of headphones or a speaker mounted to frame 12. Regardless of the implementation, earpiece 16 is configured to provide the user with audio feedback without impeding the ability of a person communicating with user to hear the speech being output by first feedback mechanism 14. In some embodiments, first and second audio devices 14, 16 are implemented together.

Figure 4:
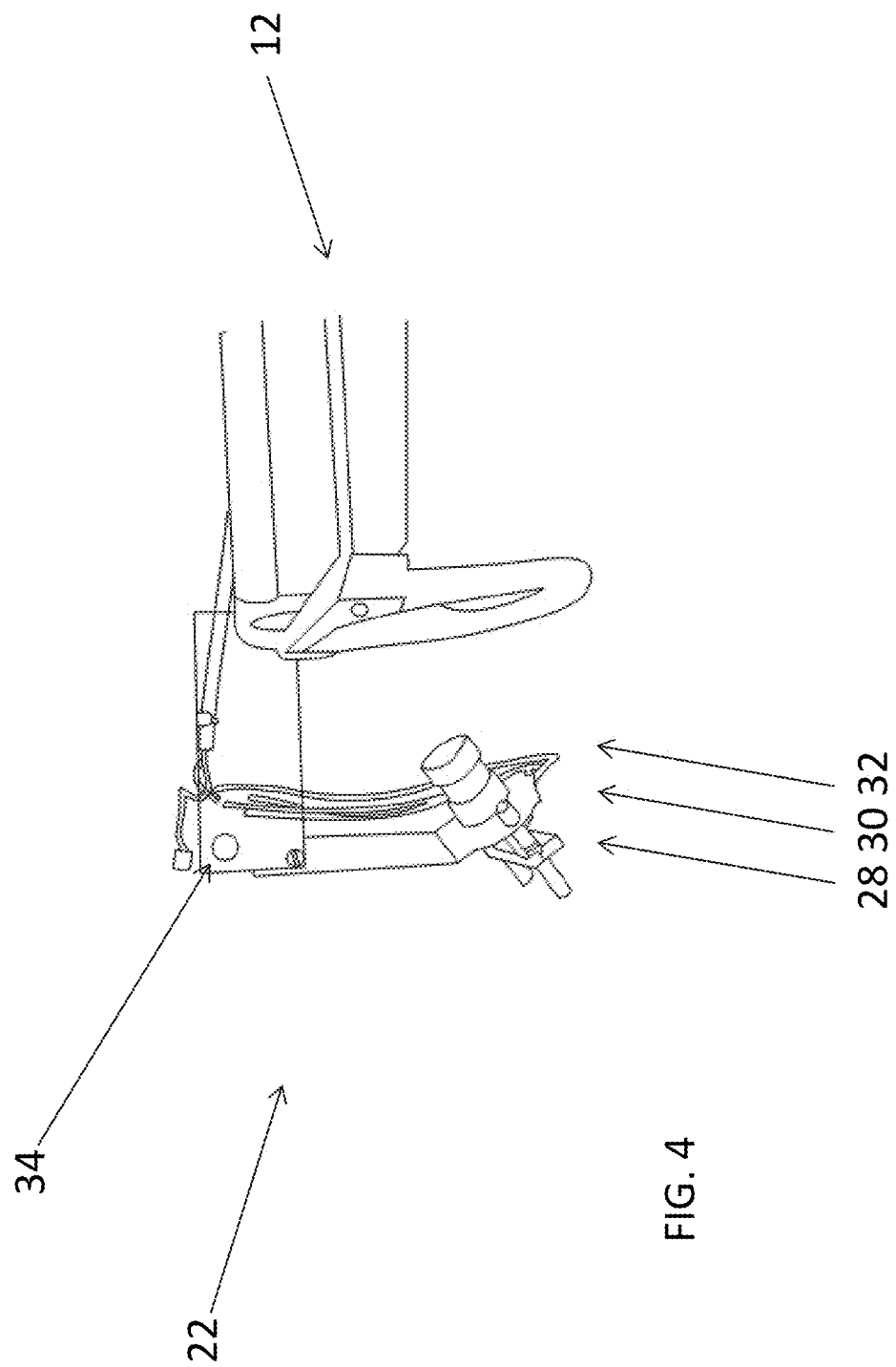
FIG. 4 illustrates one example of a communication system using infrared illumination in accordance with some embodiments.

The eye tracker 22 and optionally controller 18 are mounted on support structure 12. The eye tracker 22 is mounted close to the eyes of the user and performs gaze tracking. In some embodiments, the eye tracker 22 may be mounted 10-15 mm (depending on pupil size) from the eyes of the user. In some embodiments, infrared (IR) illumination is used in the eye tracking component, as illustrated in FIG. 4. The use of a light source in the scene enhances the quality of the image and facilitates detailed image analysis and gaze estimation. Infrared light is not visible to the human eye, so the light is comfortable for the user and does not distract attention. The device can be used at night and in low visible lighting conditions. Other modules and methods can be used to track the movement of an eye as will be understood by one of ordinary skill in the art.

FIG. 4 illustrates one example of a communication system using infrared illumination. The eye tracker may include a camera sensor 28, camera lens 30, IR band pass filter 32, and one or more IR LED's 34. One example of a camera that may be included is the Microscoft HD 6000 USB webcam, which meets the minimum requirements of providing 720p resolution and 30 frames per second (fps). In some embodiments, a thin near infrared filter is included, which delivers precise transmission of 850 nm spectral band while blocking signals at higher and lower wavelengths. These filters can be found in online filter shops and on Ebay.com. An IR LED 34 that emits a matching signal can be found at online retailers such as Vishay Intertechnology, Inc. The camera sensor 28 may be a low to medium resolution complementary metal-oxide-semiconductor (CMOS) sensor, although a high resolution device can also be utilized. In some embodiments, the sensor is connected directly to a camera interface on a controller board or via USB port, the former having an advantage of higher bandwidth. The camera lens 30 may be a macro lens supporting distances greater or less than 5 cm from the subject. The IR band pass filter 32 passes IR spectrum light through the lens to the sensor. In some embodiments the filter passes 860 nm wavelength. However, anything in the 700 nm to 1 mm range can be used. One or more IR LEDs 34 illuminate the pupil position to give a clear image of the dark pupil. While IR is described herein, the invention is not limited to the IR spectrum.

In some embodiments, the power supply is a battery 20, such as a 5 V Lithium Ion rechargeable battery. The battery 20 is used to power the system. Other power supplies can also be used as will be understood by one of ordinary skill in the art.

Figure 5A:
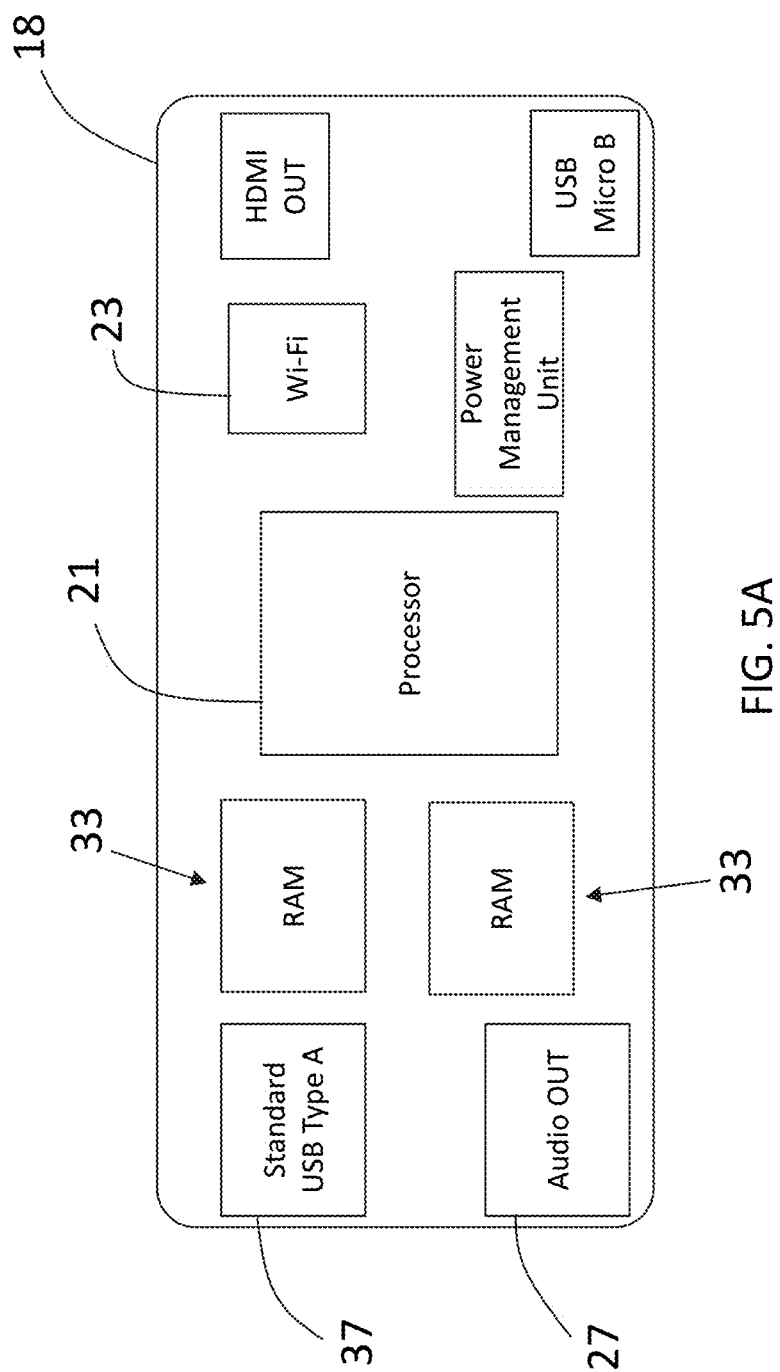
FIG. 5A is a top-plan view of a controller board used in a communication system in accordance with some embodiments.
Figure 5B:
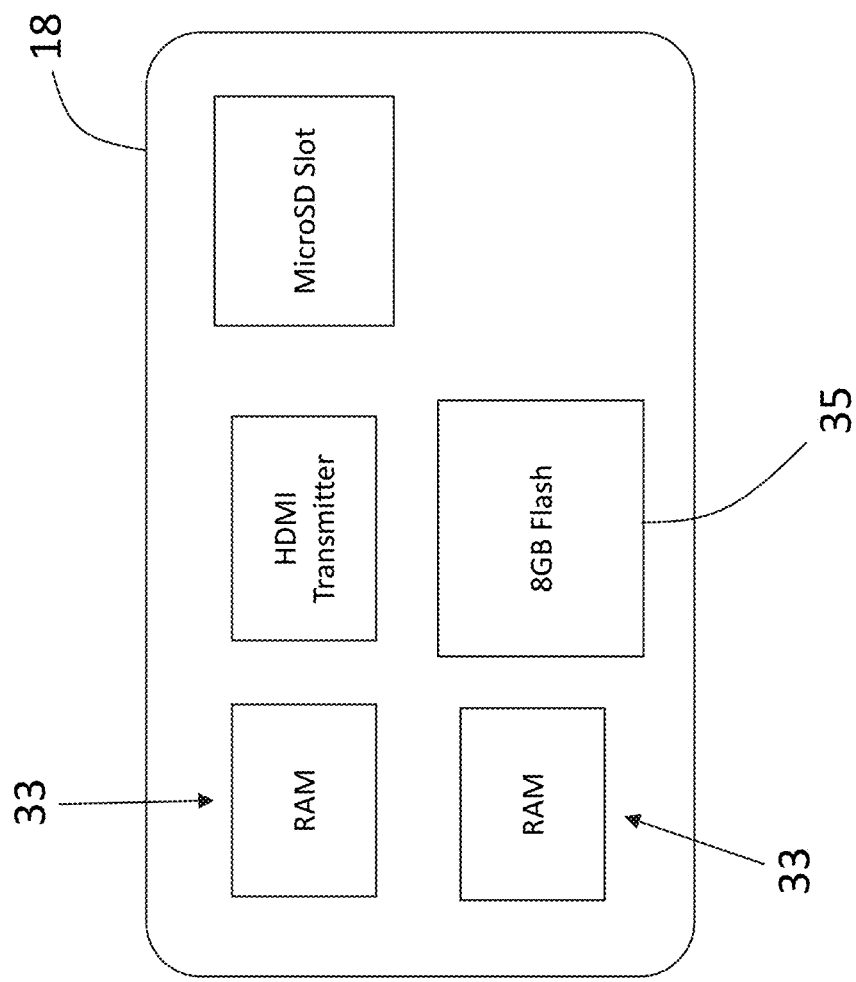
FIG. 5B is a bottom-plan posterior view of a controller board used in a communication system in accordance with some embodiments.

FIGS. 5A-B are top and bottom plan views of a controller board 18 used in a communication system in accordance with some embodiments. In some embodiments, a System on Chip (SOC) board with a dual-core Advanced RISC Machine (ARM) CPU is used to run the software and interface with other peripherals such as the camera sensor 28, second feedback mechanism 16, first feedback mechanism 14, and LED's. However, one of ordinary skill in the art will appreciate that other types of processors, CPUs, and computational devices can be used. The controller board 18 can run an Android Operating System or other operating systems, such as IOS or Windows or Embedded Linux operating systems. As shown in FIG. 2, the controller 18 comprises a dual core processor 21, a WiFi chip 23, a camera interface 25, an audio interface 27, a Bluetooth chip 29, a general purpose input/output pin 31, a first memory 33, a second memory 35, a USB port 37, a USB On the Go port 39, and a power port 41.

In some embodiments, the software is developed in Android Java and C/C++ programming languages. Standard drivers for connecting to peripherals are available in both Android and Linux environments. However, other programming languages can be used.

Figure 6:
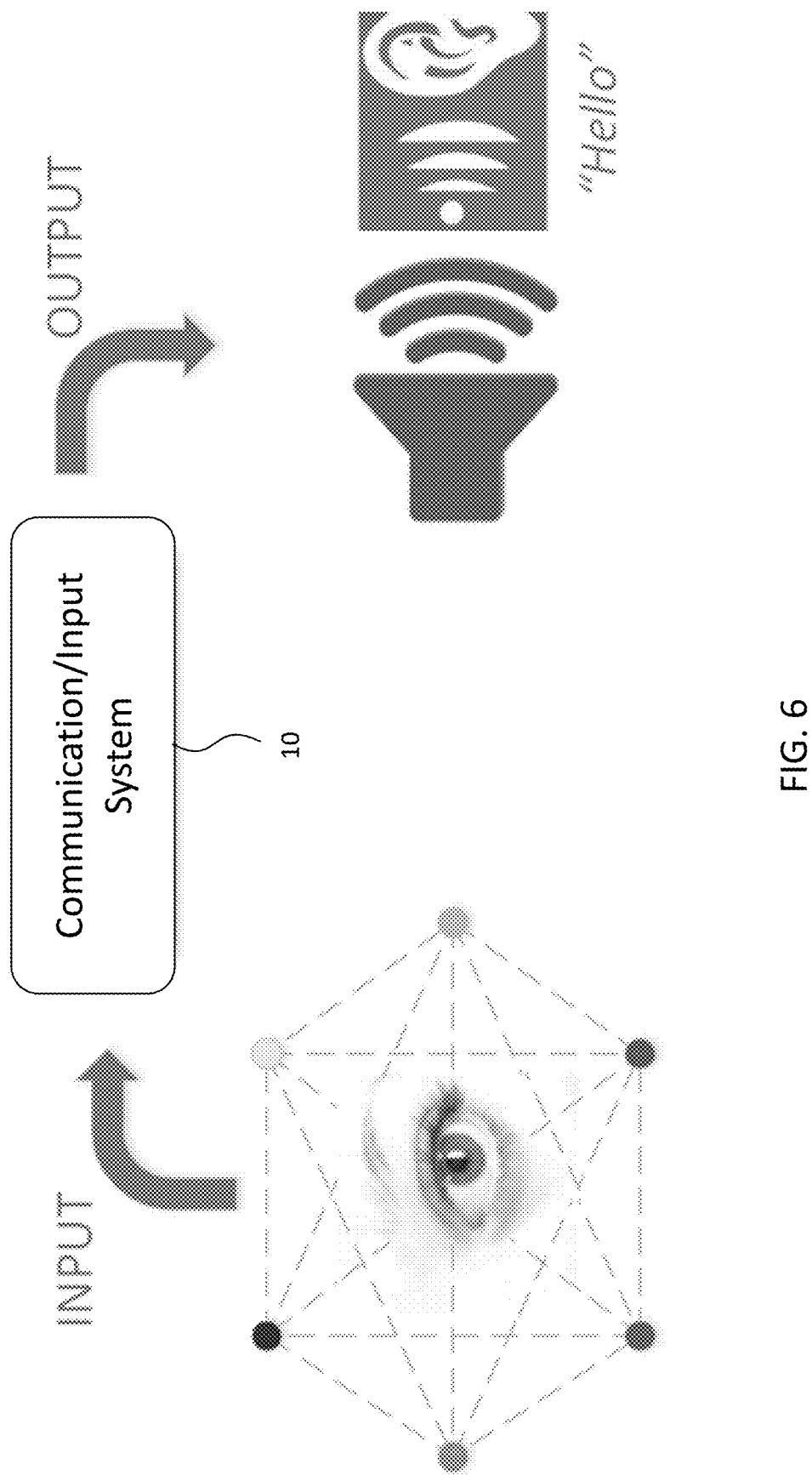
FIG. 6 is a flow diagram of one example of a method of communicating in accordance with some embodiments.
Figure 7:
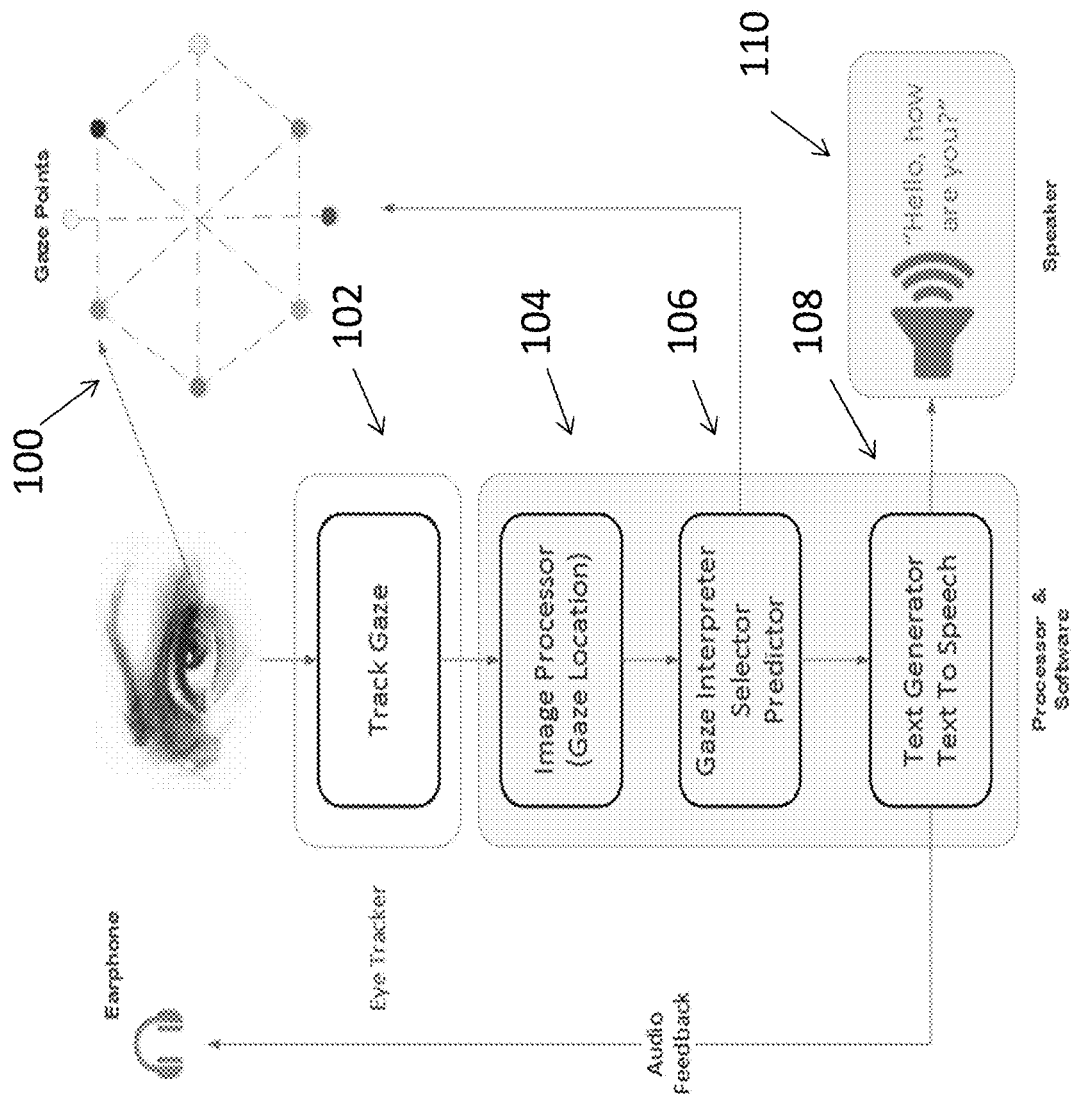
FIG. 7 is a flow diagram of one example of a method of communicating in accordance with some embodiments.

As illustrated in FIG. 6, the communication system uses eye movements as input to generate speech or text as output in some embodiments. One example of a method of using the communication system 10 is illustrated in FIG. 7. As shown in FIG. 7, at block 100, a user gazes towards one or more gaze points 24 or directions. As described above, gaze points 24 can be stickers or markings on a support structure 12, such as a pair of glasses 38. However, in some embodiments, such gaze points are not implemented however system 10 is able to track a position of a user's pupil to assess the direction in which the user is looking as described in greater detail below.

Figure 8:
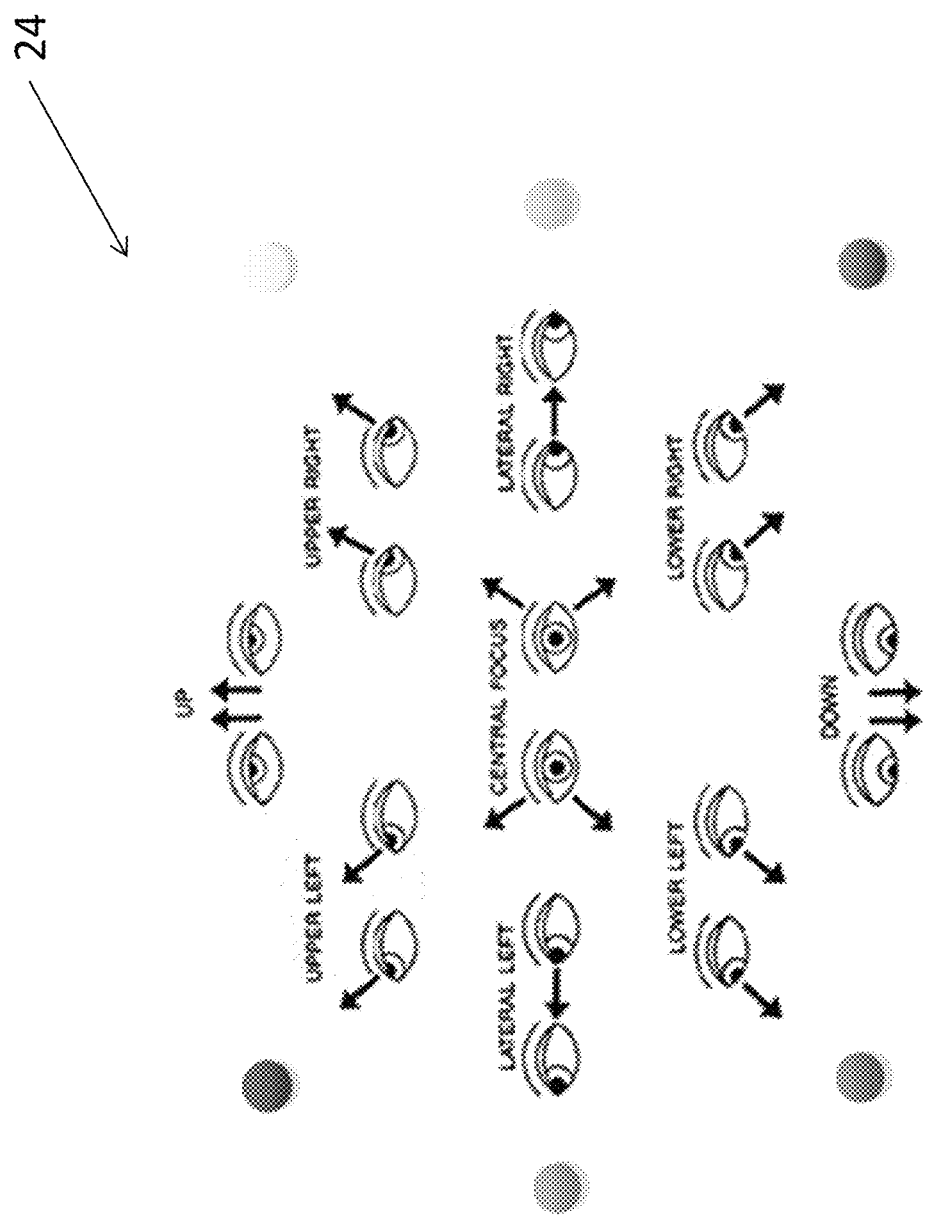
FIG. 8 illustrates one example of a method of using eye movements to input information into a communication device through gaze spots in accordance with some embodiments.
Figure 9:
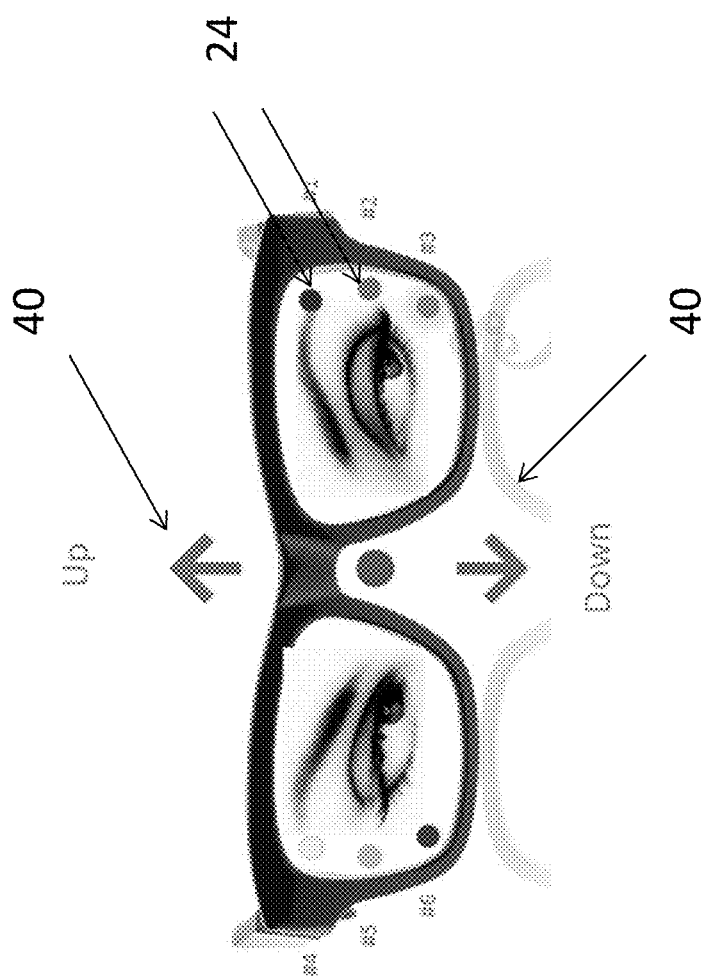
FIG. 9 illustrates one example of a method of using eye movements to input selected information into a communication device through gaze spots in accordance with some embodiments.

At block 102, an eye tracker 22 or other sensor captures the direction of the gaze. For example, As described in greater detail below, eye tracker 22 acquires image data of a user's pupil and transmits the image data to the one or more processors 21 (FIG. 2) via interface 25. FIG. 8 illustrates one example of various gaze positions that can be detected by eye tracker 22. As shown in FIG. 8, a user can look straight ahead (e.g., central focus), up, down, lateral left, lateral right, upper left, upper right, lower left, and lower right. Although nine different gazes are shown in FIG. 8, one of ordinary skill in the art will understand that eye tracker 22 can be configured to detect fewer or more gaze directions. FIG. 9 illustrates one example of gaze spots 24 being affixed to a glasses frame 38 in accordance with some embodiments. The different gaze spots 24 shown in FIG. 9 correspond to the different gaze directions shown in FIG. 8.

At block 104, the one or more processors 21 of controller 18 receives the captured image data and processes the acquired image data to identify a gaze location, i.e., a direction in which the user is looking based on a size and shape of the user's pupil. Examples of such processing techniques are described in greater detail below.

Figure 10:
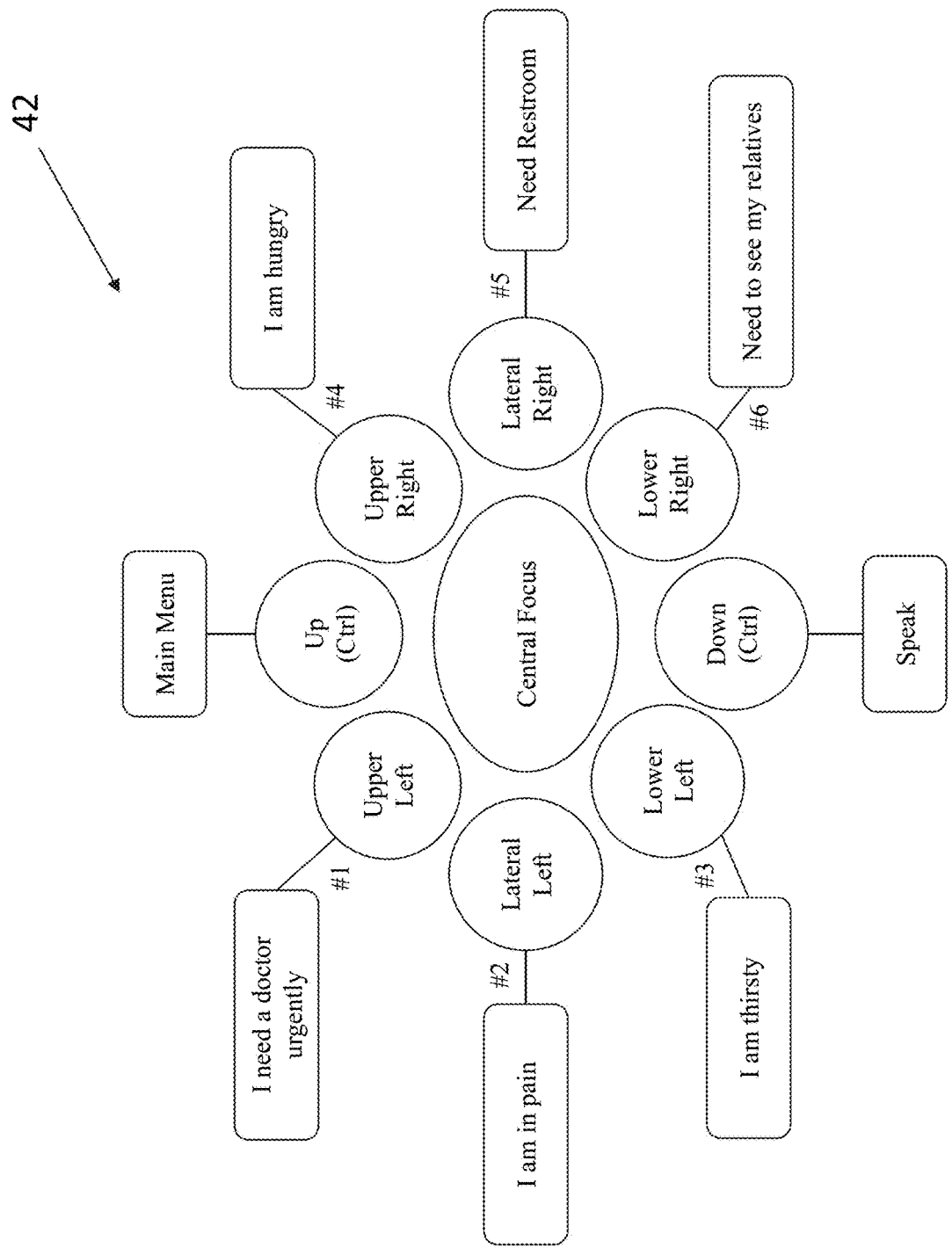
FIG. 10 illustrates one example of a communication board with predefined sentences in accordance with some embodiments.

At block 106, the one or more processors 21 of controller 18 maps the computed gaze direction to a selection of one or more predetermined input options. For example, FIG. 10 illustrates one example of a communication board 44 with predefined sentences corresponding to different gaze directions in accordance with some embodiments. The mapping between a gaze direction and a predefined sentence is performed by the one or more processors 21 of controller 18. The board 42 illustrated in FIG. 10 provides a plurality of emergency sentences with each sentence corresponding to a single gaze direction. For example, the user can select the sentence "I need a doctor urgently" by gazing toward the upper left direction, or the user can select the sentence "I am hungry" by gazing toward the upper right direction.

At block 108, the one or more processors 21 of controller 18 generates a signal for providing audio feedback via a feedback mechanism 16 or other speaker on the selection. When an event is selected, such as a letter or phrase, the software relay to the user what event has been selected. When the selection has been made, processor(s) 21 cause audio signals, which can be pre-recorded and stored in a memory 33, 35, to be transmitted to speaker 14.

At block 110, the audio signals are output through feedback mechanism 14 that is coupled to the processor(s) 21 of controller 18 via a wired or wireless connection.

The user continues to make selections by gazing towards one or more spots 24 in a sequence to complete a character, word, number, sentence or action. In some embodiments, the user can choose a variety of actions such as speak, SMS, or email by looking at the correct mapping designated for each action.

In some embodiments, the communication system software is built around a framework of boards 42. A board 42 defines mappings of the gaze directions to predetermined actions that are to be initiated and/or taken by the device 10 when the user looks in a specific direction. Some sample actions include: output a sentence to speaker; add a character to a sentence; add a number to a sentence; repeat the previously output sentence; speak "Yes"; or speak selection to earpiece; to list only a few possible examples.

Figure 11:
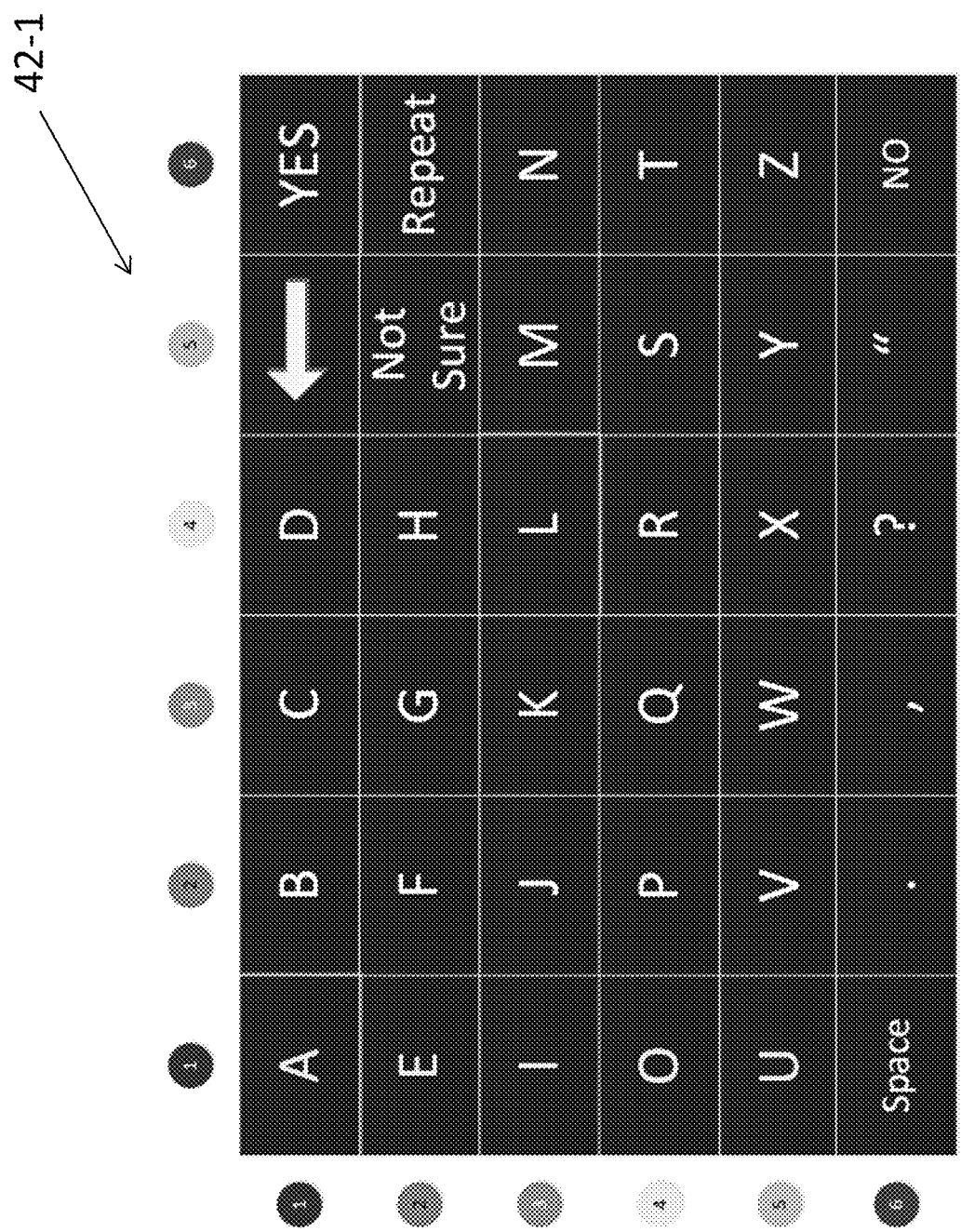
FIG. 11 illustrates one example of a communication board in accordance with some embodiments.

FIG. 11 illustrates another example of a communication board 42-1 in accordance with some embodiments. Board 42-1 provides a plurality of a letters for entering characters to form sentences. The letters of board 42-1 are selected through two gazes. In some embodiments, board 42-1 is referred to as a "vowel board" because the vowels are provided in the first column on the left in order to remember the board easily.

FIGS. 12A-12C illustrate one example of a method of using eye movements in a sequence to select the character "I" on the vowel board 42-1 of FIG. 11 in accordance with some embodiments. As shown in FIG. 11, the letter "I" is positioned in the first column and is the third letter from the top such that the letter has coordinates (3, 1).

Turning now to FIG. 12A, the user first selects the row of the letter "I", i.e., row 3, by gazing in the lower left direction as shown by the arrow. To signify that the first selection has been made, the user then provides a central focus gaze as shown in FIG. 12B. The column selection is made by providing an upper left gaze as shown by the arrow in FIG. 12C. The user will then make a central focus gaze and system 10 will output the letter 'I'.

Figure 13A:
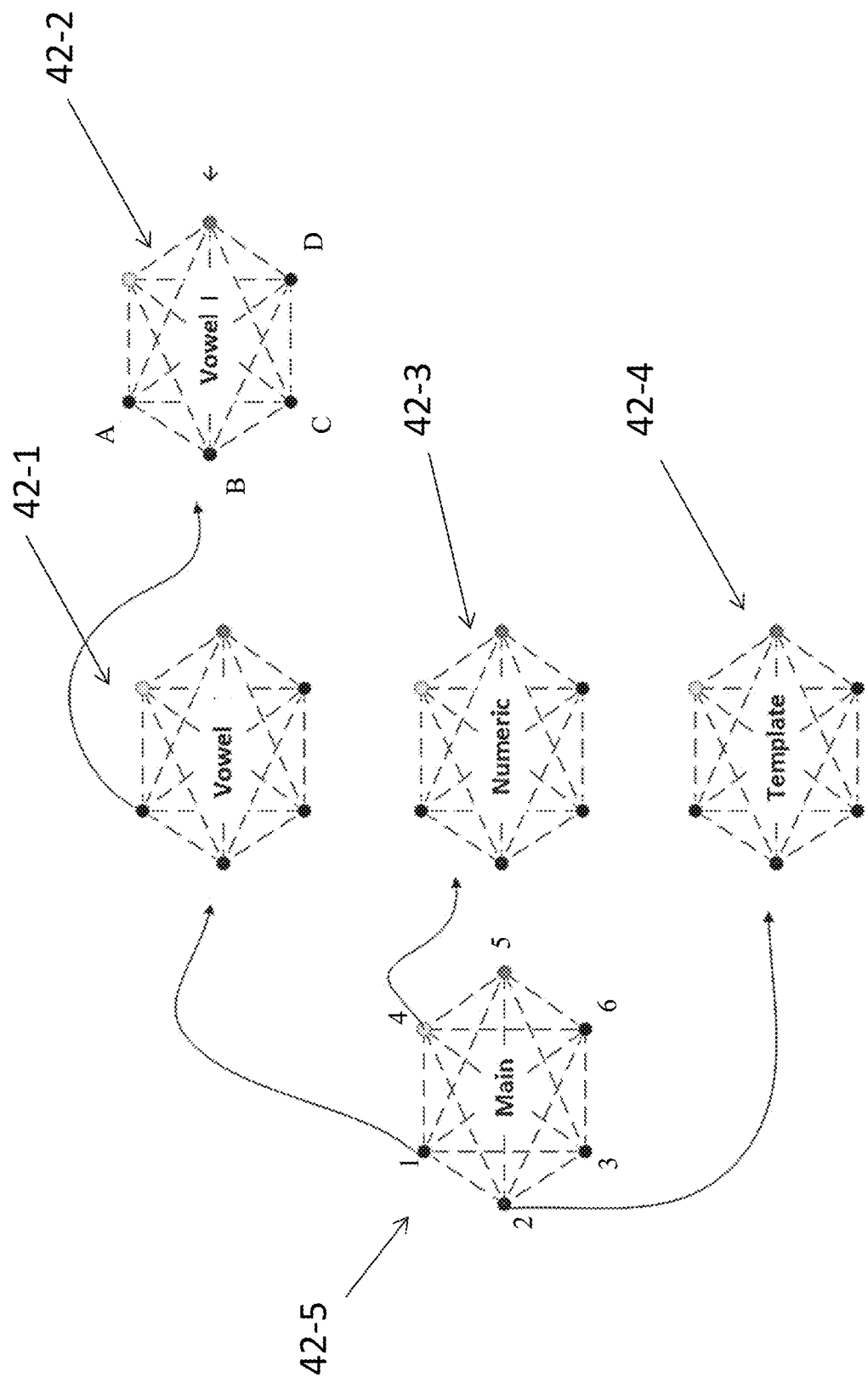
FIG. 13A illustrates one example of how a user can navigate from one communication board to another.

Numerous boards 42 can be stored in memory 33, 35 such that they are selectable by a user. As shown in FIG. 13A, numerous types of boards can be provided and a user can move from board to board using the gaze input method. Examples of such boards include, but are not limited to, one or more vowel boards 42-1, 42-2 for selecting alphabet characters; a numeric board 42-3 for selecting numbers, a sentence board for pre-defined sentences; and a template board 42-4 for sentence templates. In some embodiments, the template board 42-4 is similar to the sentence board, with the difference being that the sentences in the template board 42-4 include placeholders for users to fill in. As an example, the sentence mapped to a gaze spot 24 could be: "I need to talk to" such that the user will enter the name using the one or more vowel boards 42-1, 42-2 instead of inputting the entire sentence.

FIG. 13A further illustrates one example of a workflow of formulating sentences that involves navigating from one board 42 to another board 42. For instance, the user can initially be provided with a home or main menu board 42-5 that provides the user with the ability to select one of a plurality of boards 42. For example, a user can select the vowel board(s) 42-1, 42-2 by providing an upper left gaze at the main menu board 42-5, which then takes the user to vowel board 42-1. In some embodiments, a user can select a second vowel board 42-2 by again providing an upper left gaze when provided with vowel board 42-1. The upper left gaze when provided with vowel board 42-1 takes the user to vowel board 42-2.

Additionally or alternatively, from the main menu board 42-5, the user can select the numeric board 42-3 by providing an upper right gaze (FIG. 9), or the user can select the template board 42-4 from the main menu board 42-5 by providing a left gaze (i.e., the lateral left direction as shown in FIG. 9). Boards 42 can be configured or even created by non-technical users with the help of an easy-to-use browser-based user interface.

As mentioned briefly above, the output of a selection made on the one more boards can be generated using a text to speech (TTS) program. As will be understood by one of ordinary skill in the art, a TTS program can synthesize speech to audio devices. In some embodiments, two feedback mechanisms are provided by communication system 10 in the form of an earpiece 16 or other speaker for constant feedback on selections and prompts and an external speaker 14 for communication.

Figure 13B:
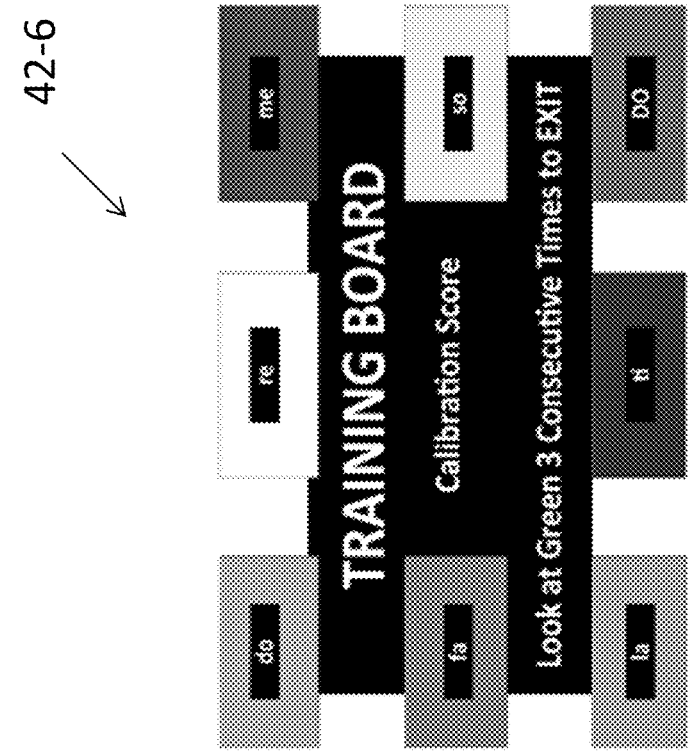
FIG. 13B illustrates one example of a secondary selection board in accordance with some embodiments in which a system uses a combination of colors and sounds (C major scale do, re, mi, fa, so, la, ti, do) to help the user memorize mappings.

In some embodiments, such as illustrated in FIG. 13B, fixed-frame-of-reference points or plurality of visual indicia 24 are mapped to corresponding frames-of-reference on a monitor or display. The colored circles or plurality of visual indicia 24 in the fixed-frame-of-reference may be colored LED lights attached to the user's eyeglass frames 38, and a training board 42-6 can be mapped to the LED lights. The system may use a combination of colors and sounds (C major scale do, re, mi, fa, so, la, ti, do) to help the user memorize mappings. For example, when the user looks at or nods towards the pink LED, i.e., an upper left gaze, the computer can interpret the user's action as selecting to play the tone "do". If the user looks at or nods towards the white LED, e.g., an upward gaze, the computer can interpret the user's action as selecting to play the tone "re".

In some embodiments a sensor, such as a camera that follows a user's gaze or an accelerometer that detects motion or some combination of the two, detects which of the eight points or LED lights attached to the user's eyeglass frames 38 the users is selecting.

Figure 13C:
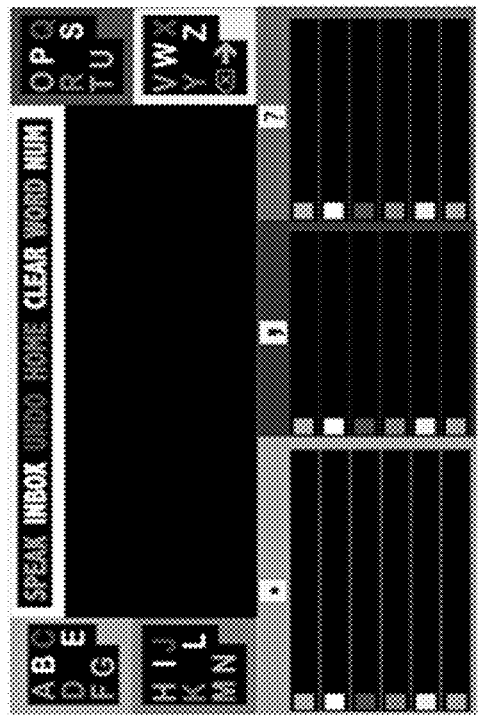
FIGS. 13C-E illustrate one example of a method of making selections using a monitor display and gaze spots in accordance with some embodiments.
Figure 13C:
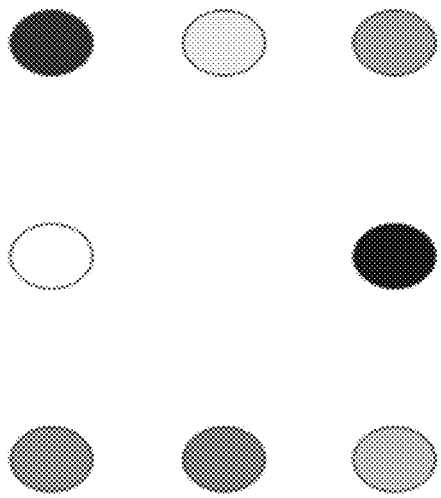

As illustrated in FIG. 13C, the user's selection from the plurality of visual indicia 24 is translated into an action/selection on a corresponding display monitor 17. If the user looked at and selected the pink LED in the upper left direction, the sensor 22 detects the selection and the processor(s) 21 of communication system 10 translates the selection into the corresponding letters in the upper left direction on the display monitor 17.

Figure 13D:
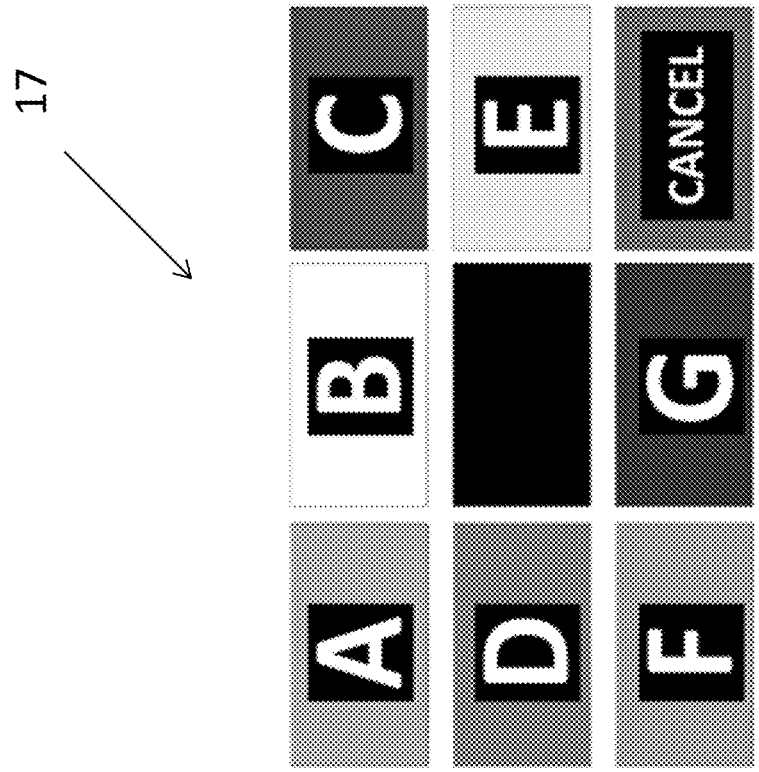
Figure 13D:
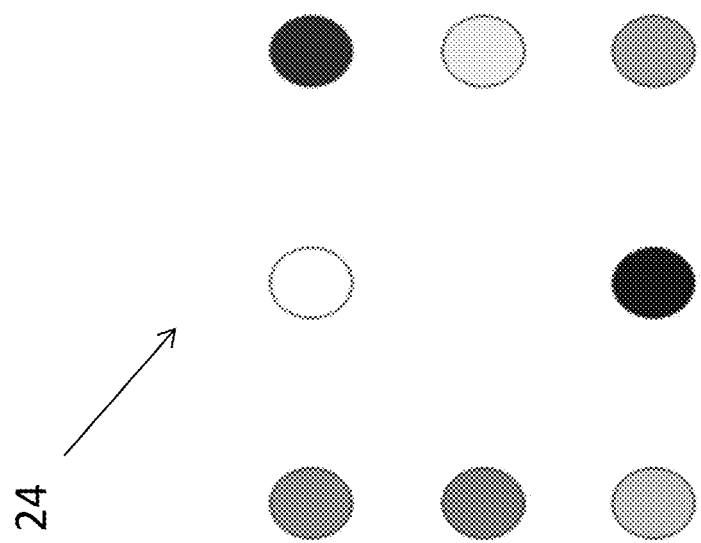

As illustrated in FIG. 13D, the monitor display 17 is then dynamically changed, while maintaining the mapping to the fixed-frame-of-reference or plurality of visual indicia 24. The user can then make a secondary selection, such as selecting the red LED in the upper right direction from the plurality of visual indicia 24 to select the letter "C".

Figure 13E:
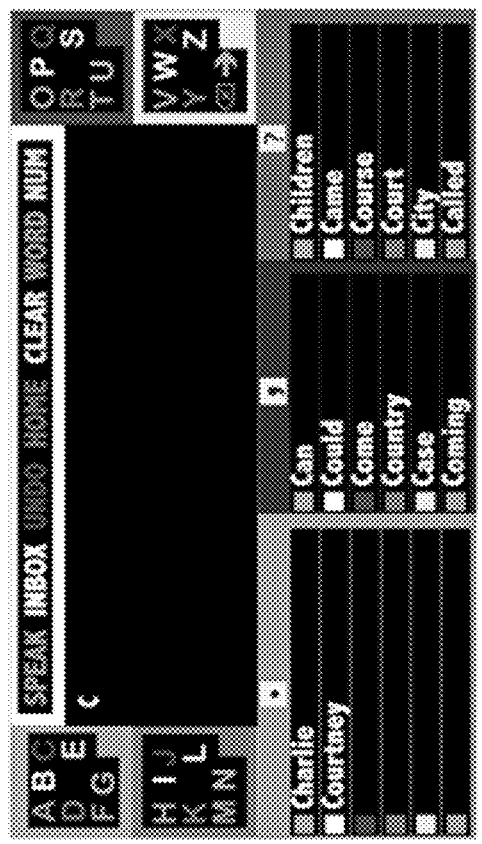
Figure 13E:
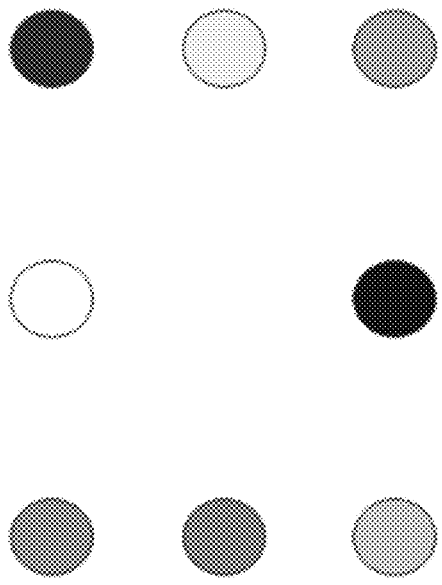

As illustrate in FIG. 13E, word completion and one-gram, bigram, trigram, four-gram and five-gram techniques can then be used to present to the user options on the monitor display 17 for quickly selecting words that we predict the user wants to input.

An auto completion and predictive word suggestion program may be included to assist users contextually in word completions, corrections and suggestions based on the characters in the current buffer. In some embodiments, user and system dictionaries are managed by this program.

In conversational speech (written or spoken), there are generally a limited number of words used to begin conversations in every language. Words that are used to begin conversations can be suggested based on the user's lexicon and who the user is writing to, such as via SMS or email. Similar logic can be applied if the user is responding to a greeting or message. The software can predict how the user will respond to messages and suggest words accordingly. Similarly, using speech recognition, the controller can suggest words predicting how the user would respond to certain spoken sentences from another person.

Once at least one character of the first word has been typed, word completion is one method to increase the user's typing speed (WPM). As the user starts typing, the Communicator can provide word predictions based on a list of the 26,000 most commonly used words in spoken English from the Corpus of Contemporary English. Based on this word list, the Communicator can suggest words that have the highest usage frequency. The suggestions can dynamically change as the user types more characters.

A list of bigrams, trigrams, four-grams and five-grams can also be obtained from the Corpus of Contemporary English. After the first word of a sentence is input using the list of 26,000 most common words, the bigram list can be examined. The second words of the top seven bigrams beginning with the input word can be selected as choices for prediction. If the user desires none of these words, he/she can input one letter of the desired word. The second words of the top seven bigrams beginning with the first word plus the newly typed character can then be offered as the new choices for completion.

Once two words have been input, the trigrams list can be examined. The procedure followed when predicting using bigrams can be applied when using trigrams as well. The top seven trigrams beginning with the two typed words can be selected and the third words can then be offered as choices for prediction. Once the user successfully inputs his third word, the same procedure can be followed with four-grams and five-grams. In some embodiment, the general rule is that when examining a list of n-grams for prediction of the next word in a sentence, the top seven n-grams beginning with the last n−1 input words in the sentence can be selected. Then, the nth words of these n-grams can be offered as choices for prediction. If the user continues typing letters of the nth word, the choices can be updated until the user's desired word appears as a choice for completion. Once more than five words have been input, predictions/completions can be continued using the n-gram list with the largest value for n but containing at least one n-gram beginning with the last n−1 words input. N is maximized in order to retain the context of the sentence. Most of the time, a larger sequence of n−1 words will narrow down the number of words that can follow it and yield predictions that are most likely to be desired by the user in the context of the phrase. In one embodiment, once the sentence exceeds five words, the five-gram list continues to be used to predict, unless the last four words of the typed sentence do not appear as the first four words in any five-gram in the list. A four-grams list can then be used, if possible, or any list with a lower value of n can be used, if a four-grams list is not possible.

Figure 14A:
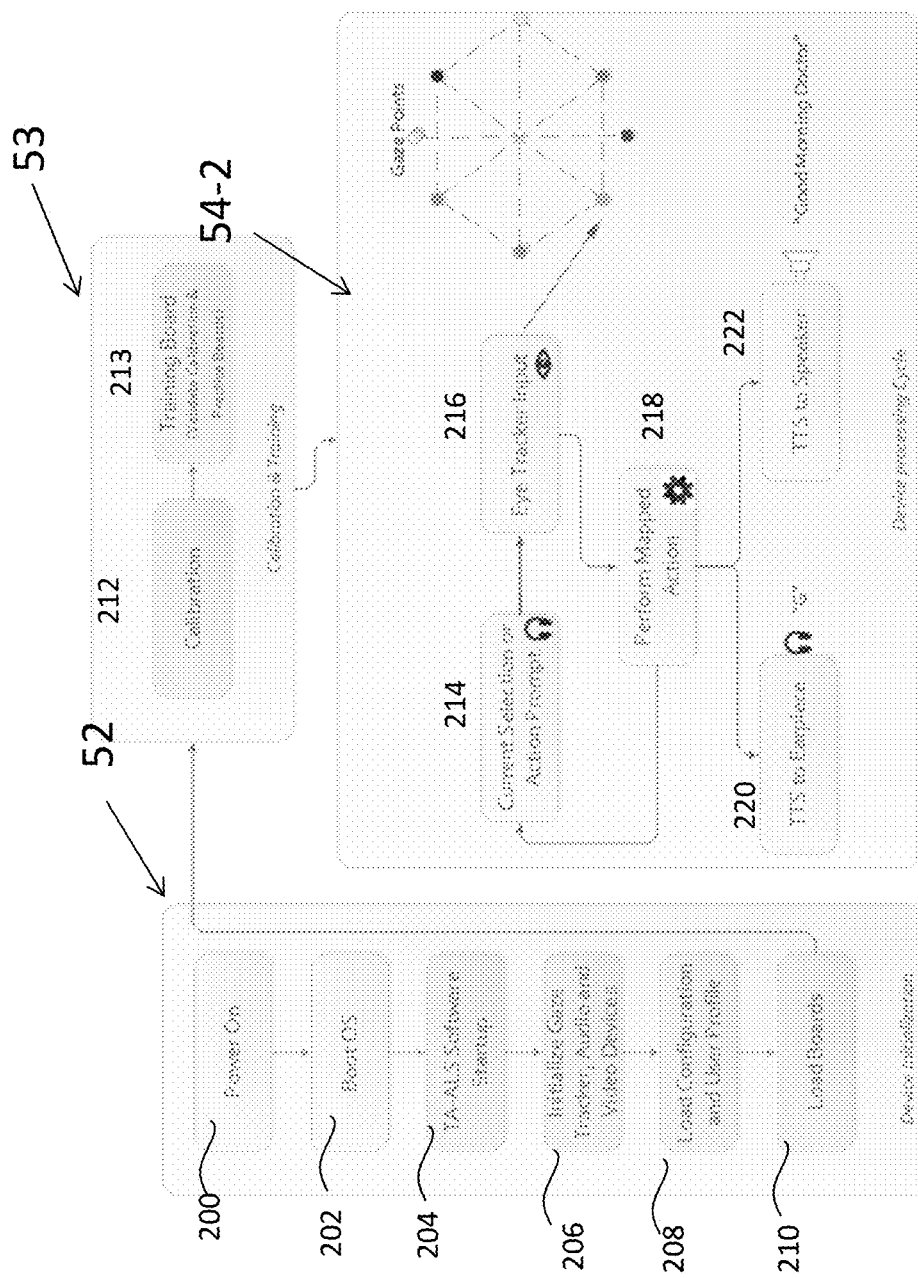
FIGS. 14A-B are flow diagrams of examples of methods of communicating in accordance with some embodiments.

FIG. 14A is a flow diagram illustrating one example of a method of operation of communication system 10 in accordance with some embodiments. The method shown in FIG. 14A includes a startup phase 52, which is executed on powering up or resetting the device, and a processing cycle phase 54-2, which loops until a pause or shutdown is intended.

The startup phase 52 begins at block 200 when the power of communication device 10 is turned on. In some embodiments, the communication system 10 is turned on in response to a user pressing a button or actuating a switch (not shown).

At block 202, the operating system is loaded from memory 35 to memory 33 and executed by the one or more processor(s) 21.

At block 204, startup scripts cause processor(s) 21 to start executing the software once operating system has been initialized.

At block 206, the processor(s) 21 executing the software checks for and initializes peripherals (eye tracker 22, feedback mechanism 16, feedback mechanism 14 and optionally Wi-Fi connectivity).

At block 208, the configuration and user profile is loaded. For example, the configuration and user profile can be retrieved from memory 35 and loaded into memory 33.

At block 210, one or more of the various boards 42 stored in memory are loaded such that they are available to a user. For example, in some embodiments, one or more of the boards stored in memory 35 are loaded into memory 33.

With the boards 42 loaded, the system 10 transitions from the initialization phase 52-2 to a calibration and training phase 53. For example, at block 212, the system 10 prompts the user to perform a calibration by asking the user to gaze at each of the spots 24 or in one or more gaze directions (center, upper left, up, down, upper right, lateral left, lateral right, lower left, and lower right).

At block 213, one or more training boards are used to validate the calibration and provides practice boards to train the user how to use system 10.

With the startup phase 52 complete, system 10 moves to the processing phase 54-1.

At block 214, the user is notified of current state and board 42. For example, system 10 may output an audio signal via feedback device 16 that reminds the user of the current board 42, i.e., "Vowel board awaiting input," or other device state.

At block 216, the user gazes or moves eyes towards one of the spots 24 or in a gaze direction to input a selection of a word, command, sentence, or other input available from the currently loaded board 42. For example and as shown in FIG. 14A, eye tracker 22 detects the user providing a lower left gaze.

At block 218, based on the position of the eye as detected by eye tracker 22, system 10 maps the position to a selection of one of the available selections of the current board 42 and provides the user with a prompt of one or more of:

(a) current selection options;
  (b) selected option;
  (c) confirmation of a selection;
  (d) current action options;
  (e) selected action; and
  (f) confirmation of an action Further, system 10 performs the selection action.

At block 220, the system 10 provides feedback to the user via feedback mechanism 16.

At block 222, system 10 provides an output, such as outputting a word or sentence via speaker 14.

Figure 14B:
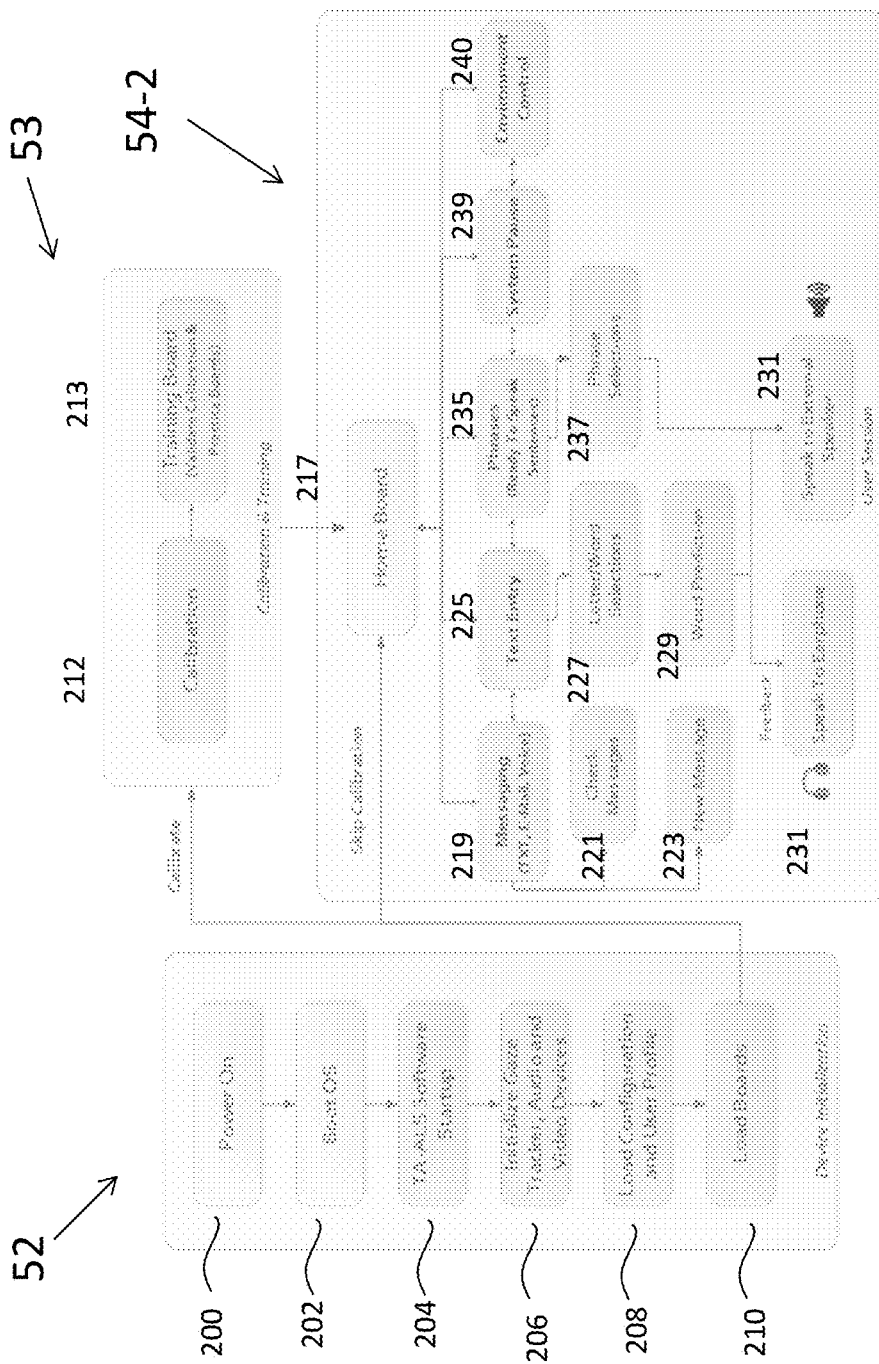

FIG. 14B illustrates another example of a method of operation of a system 10 in accordance with some embodiments. The method illustrated in FIG. 14B also includes a startup phase 52, which is executed on powering up or resetting system 10, a calibration phase 53, and a processing cycle phase 54-2, which loops until a pause or shutdown is intended.

The startup phase 52 includes the same processing blocks as described above with respect to FIG. 14A, and their descriptions are not repeated.

The method illustrated in FIG. 14B also allows the user to skip calibration phase 53 and go straight to the processing phase 54-2 at block 217 at which the user is provided with the home or main menu 42-5 board or other board that the user has selected as the landing or home board. As described above, the landing or home board can be selected and/or changed by the user at any time by selecting configuration options.

At block 219, the user can choose to access a messaging feature of the system, which can include, but is not limited to, text messaging, electronic mail, and voice mail, to list only a few possibilities.

At block 221, the user can check his/her messages, such as text messages, email messages, and/or voice mail messages.

At block 223, the user can compose a new message, such as a text message, email message, and/or voicemail message that is generated using TTS.

Alternatively from the home board 42-5, for example, the user can choose to access the text entry feature at block 225. If the text entry selection is made at block 225, then system 10 can move to block 227 and/or 229 in which the user enters character in the manner as described above with respect to FIGS. 11-12C. In some embodiments, system 10 is configured to provide word prediction at block 229 as the user selects characters as described above.

At block 231, the user is provided with feedback of the current selection or proposed word. In some embodiments, the feedback is provided on a display (not shown) or via earpiece 16 (FIGS. 1A-1E), or other audio output device as will be understood by one of ordinary skill in the art.

At block 233, the selected character or selected word is output via speaker 14 in response to user selection as shown in FIGS. 1A-1E.

Referring again to FIG. 14B, from the home board at block 217, the user can choose to access a communication board with predefined sentences at block 235.

At block 237, the gazes in a predetermined gaze direction or moves his or her eyes towards one of the gaze spots 24 to indicate a selection of a sentence or phrase as described above with respect to FIG. 10. In response to a phrase having been provisionally selected at block 237, the user is provided with feedback of the selected phrase at block 231. In some embodiments, the feedback is provided on a display (not shown) or via earpiece 16 (FIGS. 1A-1E), or other audio output device as will be understood by one of ordinary skill in the art.

At block 233, the selected phrase is output via speaker 14 as shown in FIGS. 1A-1E in response to user making a final selection.

In some embodiments, the main menu board 42-5 can also provide the user with the ability to pause the system 10 such that the movement of the user's eyes will not trigger a selection of text, characters, or other inputs. For example, as shown in FIG. 14B, the user can select to pause and unpause the device at block 239.

In some embodiments, the main menu board 42-5 can also provide the user with the ability to control and interact with the external environment. These actions could include, but are not limited to: controlling a television, controlling medical support devices such as a motorized bed or wheelchair, and controlling lights in a room. As shown in FIG. 14B, the user can select the environmental control board at block 240.

Figure 14C:
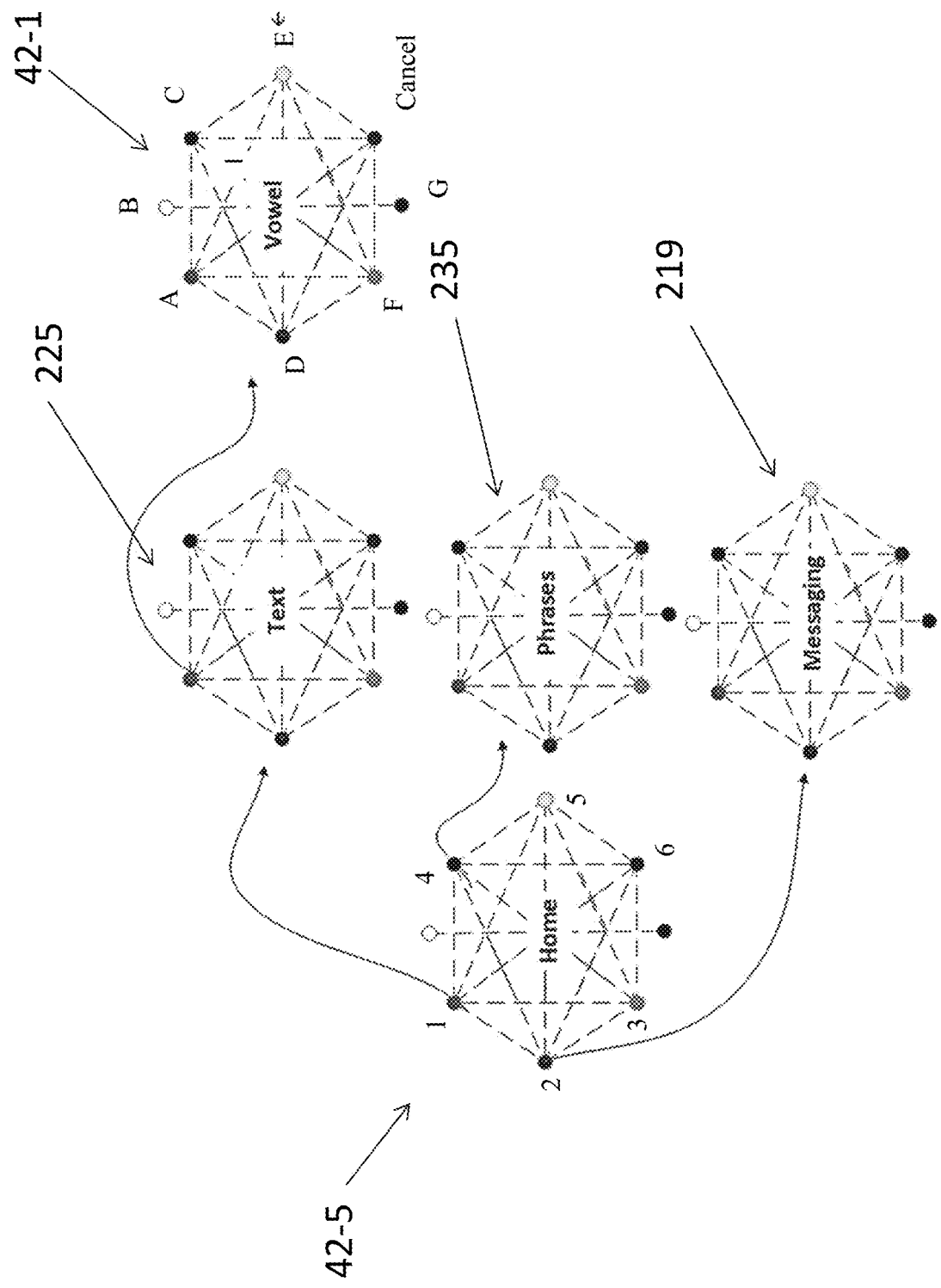
FIG. 14C illustrates one example of how a user can navigate from one feature of the system to another.

As shown in FIG. 14C, numerous types of features can be provided and a user can move from feature to feature using the gaze input method. Examples of such features include, but are not limited to, text entry feature 225; a communication feature with predefined sentences and phrases 235; and a messaging feature 219, which can include text messaging, electronic mail, and voice mail.

FIG. 14C further illustrates one example of a workflow of communicating that involves navigating from one feature to another. For instance, the user can initially be provided with a home or main menu board 42-5 that provides the user with the ability to select one of a plurality of features. For example, a user can select the text entry feature 225 by providing an upper left gaze at the main menu board 42-5, which then takes the user to text entry feature 225. In some embodiments, a user can then select a vowel board 42-1 by again providing an upper left gaze when provided with text entry feature 225. The upper left gaze at when provided with text entry feature 225 takes the user to vowel board 42-1.

Additionally or alternatively, from the main menu board 42-5, the user can select the communication feature with predefined sentences and phrases 235 by providing an upper right gaze (FIG. 9), or the user can select a messaging feature 219 from the main menu board 42-5 by providing a left gaze (i.e., the lateral left direction as shown in FIG. 9).

Certain activities may be performed by a support person. Such activities include positioning the device in front of the user, turning the device on, performing one-time, initial adjustments, as well as starting a first self-guided tutorial, and possibly resetting the device. Access to activities that can be automated to a large extent should be simplified to the extent possible, e.g., a dedicated button can be provided to turn power to the device on and off, reset the device, and start the self-guided tutorial, respectively.

Figure 15:
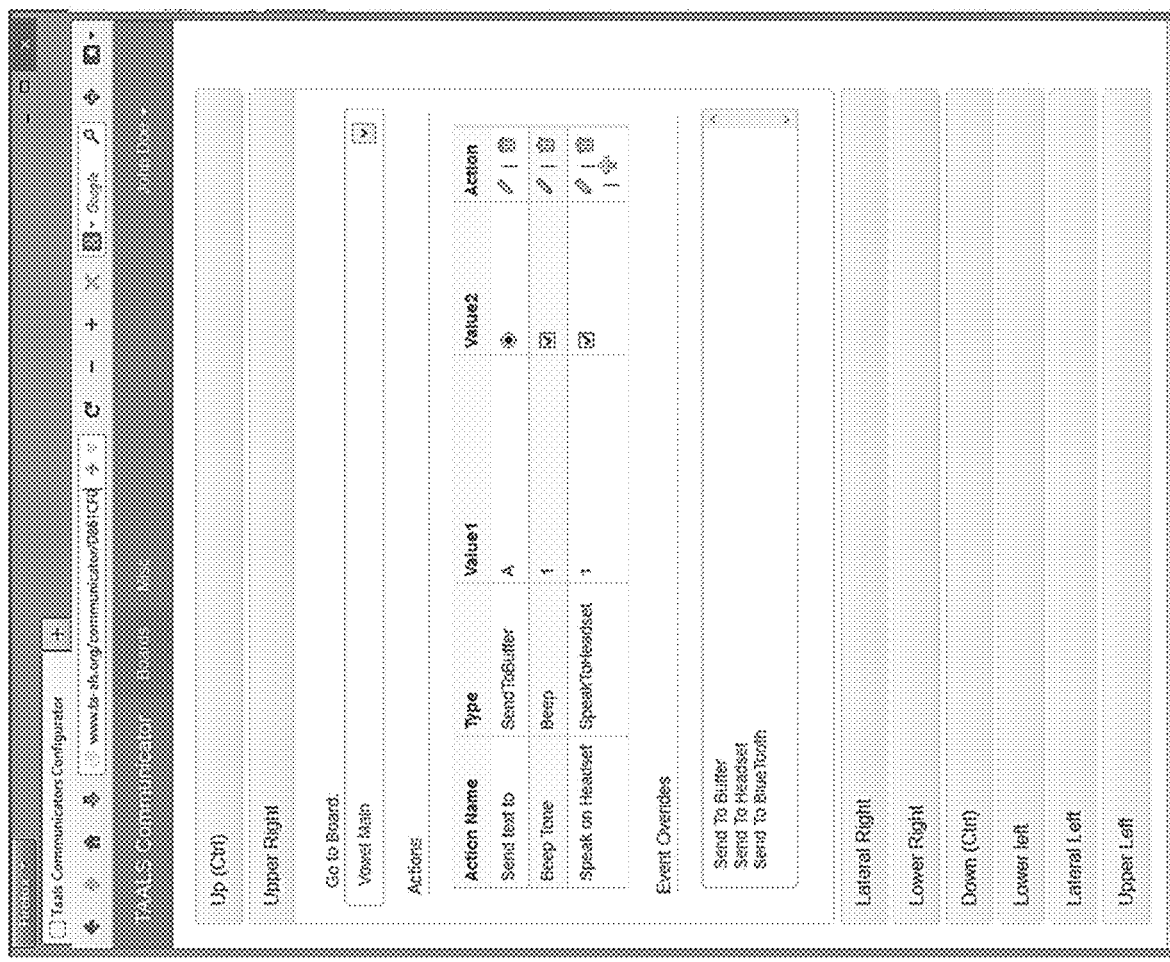
FIG. 15 illustrates one example of a web user interface connected to a communication device, which allows users to customize boards, actions, and events in accordance with some embodiments.

Existing boards 42 can be modified and/or new boards can be uploaded to the device by connecting a browser on a desktop/mobile to the web server running on the device. Uploading a new board includes mapping text to speak, audio feedback to provide, and optionally a next board to navigate to each of the spots on the board. FIG. 15 illustrates one example of an internet browser connected to a communication device for managing boards and other device settings in accordance with some embodiments. The internet browser is a user interface that gives a user or caregiver complete control over the software. For example, the user can customize the pre-loaded phrases to phrases that better suit him/her. Selecting a phrase is an example of an event. A user can also customize actions, which tell the program what it should do when an event is selected. For example, when a phrase or event is selected, the user can choose whether he/she wants the phrase to be spoken from the speaker or if he/she wants to hear it first via an earpiece before confirming that it should be spoken out loud. As shown in FIG. 15, the user can configure what words, phrases, or characters correspond to certain gazes to provide customized boards. Further, the user can select certain action that are to be performed in response to certain gazes on certain boards, and also have the ability to adjust the type of feedback to be provided, if any.

The software of system 10 may also include training programs that allows users to learn to use the device and practice to achieve higher speech rates. User can also fine-tune the workings of the device in training mode as well as build vocabulary, shortcuts and pre-defined sentences.

Figure 16:
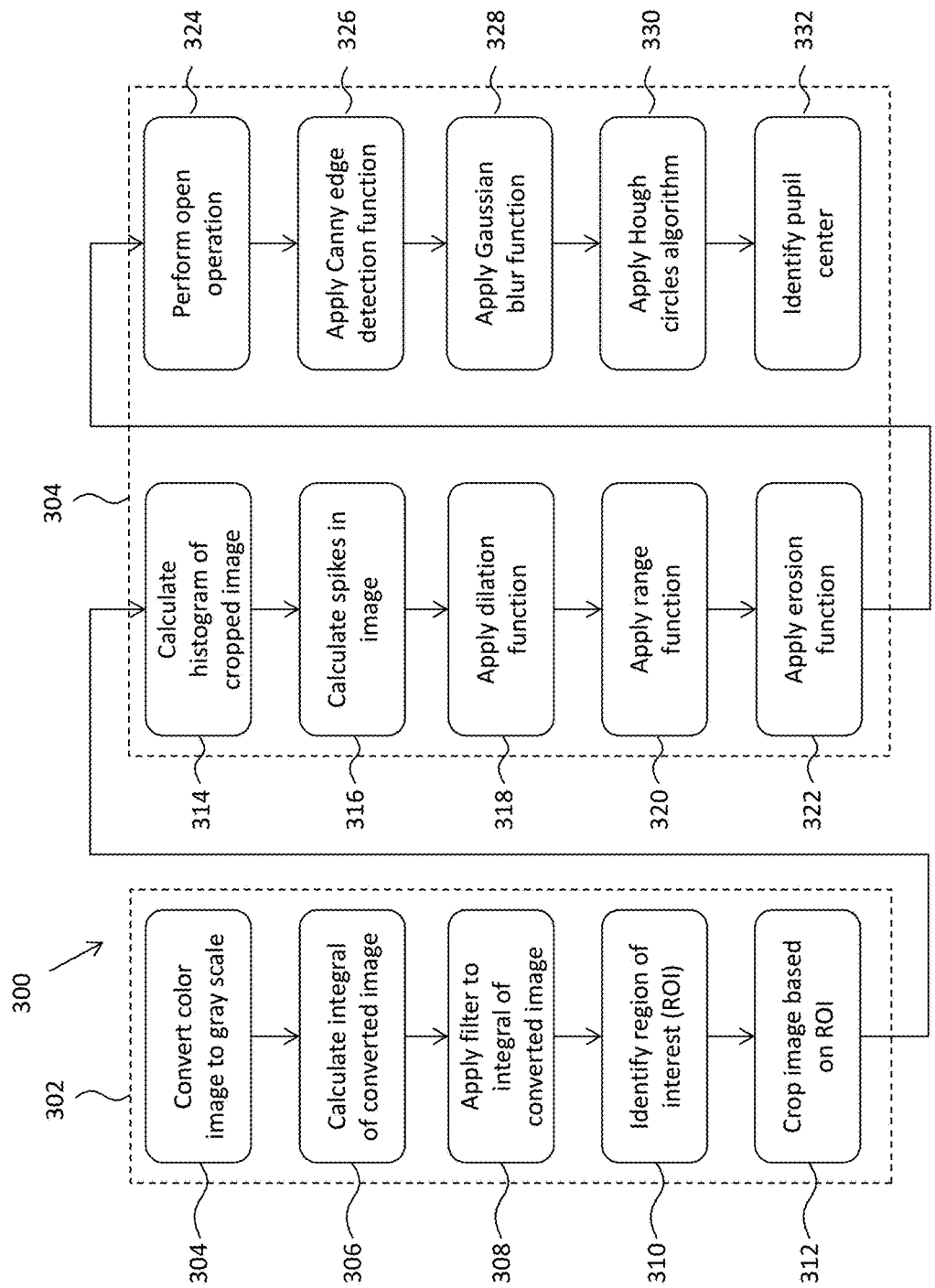
FIG. 16 is a flow diagram of algorithms that can be used to track eye movement in accordance with some embodiments.

FIG. 16 illustrates one example of a gaze tracking algorithm 300 performed by system 10 in accordance with some embodiments. In some embodiments, the gaze tracking algorithm includes two phases: an image cropping phase, which detects the approximate position of a pupil and crops the original image acquired by sensor 24, and a circle detection phase 304 that is used to determine the position and center of the pupil that corresponds to the user's gaze. In some embodiments, gaze tracking algorithm 300, including phases 302 and 304, are performed by processors 21 in response to instructions stored in a memory, such as memory 33 and/or 35, and signals received from eye tracker module 22.

At block 302, the image cropping algorithm is performed.

At block 306, the input color image is converted from YUV to gray scale format. YUV to Grayscale Conversion is done by an OpenCV function of the ImgProc package which converts an image from one color space to another. This can be found at, for example, http://docs.opencv.org/modules/imgproc/doc/miscellaneous_transformatiops.html#cvtcolor, which is incorporated by reference herein in its entirety. For example, the image data received from eye tracker module 22 is received at processor(s) 21 in YUV format and is converted to a gray scale format.

At block 308, the integral of the gray scale formatted image data is calculated. this is an internal OpenCV function of the ImgProc package. The integral is calculated using the following equation, which can be found at http://docs.opencv.org/modules/imgproc/doc/miscellaneous_transformations.html#integral, and is incorporated by reference herein in its entirety:

$$\text{sum}(X,Y) = \Sigma_{x<X, y<Y} \text{image}(x,y)$$

In some embodiments, the integral is an image where the value of each pixel is the sum of the values of the pixels above and to the left of it.

At block 310, a filter function is run on the calculated integral to locate the approximate position of the pupil based on the darkest pixel concentration. The filter function segregates the pixels according to their intensity and finds the largest concentration of dark pixels, assuming this to be the pupil. The resulting image is stored in the form of a matrix object. This matrix is what is being filtered. The filter function should return three values: the X & Y coordinates from where cropping should start and the width of the resultant image. This resultant image serves as the region of interest (ROI) on which further processing is applied.

At block 312, the resultant image is cropped based on the approximate values returned by the filter function.

With the image having been cropped, a circle detection algorithm is performed at block 304.

At block 314, a histogram of the cropped image is calculated. In some embodiments, the histogram is calculated using an internal OpenCV function calcHist( ) which computes the pixel distribution of the input array between the range of 0-256.

At block 316, the lowest and highest spike in the image are determined based on the histogram calculated at block 314. In some embodiments, these calculated values can be used in one or more morphology functions as described below.

At block 318, dilation functions are applied to the image with a mask. Dilation increases the brighter parts of the image. It is a procedure used to remove unwanted noise from an image. In some embodiments, the mask is a 7×7 mask; however, one of ordinary skill in the art will understand that other masks can be applied.

At block 320, a range function is used to determine whether the image elements lie within the highest spike. The range function checks if array elements lie between the elements of two other arrays. The highest spike is the pixel that has the highest concentration (number) of pixels in the image. The function checks the range as follows:

For every element of a single-channel input array, the following formula is used: dst(I)=lowerb(I)_0<=src(I)_0<=upperb(I)_0

For two-channel arrays, the following formula is used: dst(I)=lowerb(I)_0<=src(I)_0<=upperb(I)_0 land lowerb (I)_ I<=src(I)_I<=upperb(I)_I That is, dst (I) is set to 255 (all 1-bits) if src (I) is within the specified 1D, 2D, 3D, etc. box and 0 otherwise.

When the lower and/or upper boundary parameters are scalars, the indexes (I) at lowerb and upperb in the above formulas should be omitted.

The parameters are as follows:

src—first input array.

lowerb—inclusive lower boundary array or a scalar.

upperb—inclusive upper boundary array or a scalar.

dst—output array of the same size as src and CV_8U type.

At block 322, an erosion function is applied to the masked image to remove the excess noise.

At block 324, an open operation is performed to at least partially ignore and/or remove any eyelashes or other irrelevant objects that may be present in the received image data. In some embodiments, the open operation is performed using the combination of two OpenCV functions: getStructuringElement( ), which returns a structuring element of the specified size and shape for morphological operations and morphologyEx( ), which performs advanced morphological transformations.

At block 326, a Canny edge detection function is applied to the image to find all the edges within which lies the pupil.

At block 328, a Gaussian blur function is applied to the image to smooth the image. In some embodiments, the image is blurred using a Gaussian filter of kernel size 5×5; however, one of ordinary skill in the art will understand that other kernel sizes can be used.

At block 330, a Hough Circles algorithm is applied to the gray scale image to detect circles having a radius within a predetermined range. In some embodiments, the predetermined range is 10-35 pixels; however, one of ordinary skill in the art will understand that other ranges can be used.

At block 332, the pupil center is identified based on the size of the circles determined by the algorithm 330. At this point no further calculations are required. The center is returned to the main algorithm (to proceed with event detection).

The disclosed systems and methods described herein advantageously provide users with the ability to communicate with others and/or provide inputs and commands to other systems. In some embodiments, for example, the disclosed systems and methods provide low-cost, portable, standalone AAC devices that enables patients with ALS or other disabilities or impairments to communicate, i.e., by generating speech or text. The disclosed systems and methods are extendible to provide users with the ability to provide inputs in a variety of ways including, but not limited to, moving an eye, breathing in certain directions, or other movement of a human body excluding an appendage such as a hand, foot, or limb. In some embodiments, the disclosed systems and methods advantageously enable speech rates, in one or more languages, between 15-20 words per minute ("WPM") using suggestions, completions, and templates based on computer algorithms and preloaded dictionaries.

The disclosed methods can be at least partially embodied in the form of program code embodied in tangible media, such as floppy diskettes, CD-ROMs, DVD-ROMs, Blu-ray disks, hard drives, solid state drives, Flash memory, or any other non-transitory machine-readable storage medium, wherein, when the program code is loaded into and executed by a machine, such as a processor, the machine becomes an apparatus for practicing the method. The disclosed methods also can be at least partially embodied in the form of program code, for example, whether stored in a storage medium, loaded into and/or executed by a machine, or transmitted over some transmission medium, such as over electrical wiring or cabling, through fiber optics, or via electromagnetic radiation, wherein, when the program code is loaded into and executed by a machine, such as a computer, the machine becomes an apparatus for practicing the method. When implemented on a general-purpose processor, the program code segments combine with the processor to provide a unique device that operates analogously to specific logic circuits.

Although the disclosed systems and methods have been described in terms of exemplary embodiments, they are not limited thereto. Rather, the appended claims should be construed broadly, to include other variants and embodiments of the disclosed systems and methods, which may be made by those skilled in the art without departing from the scope and range of equivalents of the systems and methods.

What is claimed is:

1. A system, comprising:
   a support structure supporting a plurality of visible indicia;
   a feedback mechanism, the feedback mechanism configured to provide at least one of visual feedback and audio feedback;
   a sensor supported by the support structure, the sensor configured to identify a position of a pupil of an eye of a user; and
   a controller communicatively coupled to the sensor and to the feedback mechanism, the controller configured to:
      receive a first signal from the sensor, the first signal indicative of a gaze direction of the pupil,
      identify, based on the first signal, a gazed upon visible indicia of the plurality of visible indicia, the gazed upon visible indicia being the visible indicia that most closely corresponds to the gaze direction,
      map the gazed upon visible indicia to a virtual reference frame, the virtual reference frame comprising a plurality of members of a set,
      identify a selected member from the plurality of members of the set,
      cause the feedback mechanism to notify the user that the selected member has been identified,
      update the virtual reference frame if the selected member is not one of a group of predetermined final selections, and
      transmit a second signal to at least one of the feedback mechanism and a first device to initiate an action based on the selected member if the selected member is one of the group of predetermined final selections.

2. The system of claim 1, wherein the notification that the selected member has been identified includes at least one of changing a brightness of at least one of the plurality of visible indicia and blinking at least one of the plurality of visible indicia.

3. The system of claim 2, wherein changing the brightness of at least one of the plurality of visible indicia includes gradually increasing the brightness of the at least one of the plurality of visible indicia.

4. The system of claim 1, wherein the support structure includes a frame which supports an infrared light source for illuminating the eye.

5. The system of claim 1, wherein the feedback mechanism includes at least one of a speaker, an earpiece, a mounted heads-up display, and a visual display.

6. The system of claim 1, wherein the support structure includes glasses for being worn by the user.

7. The system of claim 6, wherein the support structure further includes an arm coupled to the glasses and extending in front of the glasses, wherein the sensor includes a camera, and wherein the arm supports the camera such that, when the glasses are worn by the user, a lens of the camera is facing toward at least one of the user's eyes.

8. The system of claim 7, wherein the support structure further includes a housing coupled to the glasses, wherein the controller is disposed in the housing, and wherein the arm is coupled to and extends from the housing.

9. The system of claim 1, wherein the feedback mechanism includes a visual display, and wherein the visual display is configured to display a representation of the virtual reference frame.

10. The system of claim 1, wherein the group of final selections includes at least one of a letter, a number, a word, a phrase, and a sentence.

11. The system of claim 1, wherein the controller is configured to transmit the second signal to the first device if the selected member is one of the group of final selections, and wherein the first device is selected from the group consisting of a television, a medical support device, and a light.

12. The system of claim 1, wherein the first device is a speaker, and wherein the controller transmits the selected member to the speaker if the selected member is one of the group of final selections such that the speaker broadcasts the selected member.

13. A method, comprising:
   receiving, by a processor, a first signal from a sensor, the first signal indicative of a gaze direction of a pupil of an eye of a user gazing at at least one of a plurality of visible indicia;
   identify, based on the first signal, a gazed upon visible indicia, the gazed upon visible indicia being one of the plurality of visible indicia;
   mapping, by the processor, the gazed upon visible indicia to a virtual reference frame, the virtual reference frame comprising a plurality of members of a set;
   identifying a selected member from the plurality of members of the set;
   causing a feedback mechanism to provide visual or audio feedback that the selected member has been identified;
   updating the virtual reference frame if the selected member is not one of a group of predetermined final selections; and
   transmitting a second signal to the feedback mechanism or to a first device to initiate an action based on the selected member if the selected member is one of the group of predetermined final selections.

14. The method of claim 13, further comprising adjusting a brightness of at least one of the plurality of visible indicia in response to identifying the selected member.

15. The method of claim 14, wherein adjusting the brightness of at least one of the plurality of visible indicia includes gradually increasing the brightness.

16. The method of claim 13, further comprising causing at least one of the plurality of visible indicia to blink in response to identifying the selected member.

17. The method of claim 13, wherein the second signal is transmitted to the first device, the first device includes a controllable device, and the method further comprises causing the controllable device to perform a function in response to receiving the second signal.

18. A system, comprising:
a support structure comprising glasses and an arm coupled to the glasses and extending in front of the glasses;
a plurality of visible indicia supported by the support structure;
a feedback mechanism, the feedback mechanism configured to provide at least one of visual feedback and audio feedback;
a sensor configured to identify a position of a pupil of an eye, the sensor including a camera, wherein the camera is supported by the arm of the support structure such that, when the glasses are worn by a user, a lens of the camera is facing toward at least one of the user's eyes; and
a controller communicatively coupled to the camera and to the feedback mechanism, the controller configured to:
receive a first signal from the camera, the first signal indicative of a gaze direction of the pupil,
identify, based on the first signal, a gazed upon visible indicia, the gazed upon visible indicia being one of the plurality of visible indicia that most closely corresponds to the gaze direction,
map the gazed upon visible indicia to a virtual reference frame, the virtual reference frame comprising a plurality of members of a set,
identify a selection of one of the plurality of members of the set, and
transmit a second signal to the feedback mechanism or to a first device to initiate an action based on the selection.

19. The system of claim 18, wherein the plurality of visible indicia are affixed to a lens of the glasses.

20. The system of claim 18, wherein the support structure further includes a housing coupled to the glasses, wherein the controller is disposed in the housing, and wherein the arm is coupled to and extends from the housing.

* * * * *